(12) United States Patent
Houck et al.

(10) Patent No.: US 8,012,934 B2
(45) Date of Patent: Sep. 6, 2011

(54) SMALL PEPTIDES AND METHODS FOR TREATMENT OF INFLAMMATION

(75) Inventors: John C. Houck, Seattle, WA (US); James Clagett, Snohomish, WA (US)

(73) Assignee: Mowycal Lending, LLC, Big Horn, WY (US)

( * ) Notice: Subject to any disclaimer, the term of this patent is extended or adjusted under 35 U.S.C. 154(b) by 1902 days.

(21) Appl. No.: 10/147,633

(22) Filed: May 16, 2002

(65) Prior Publication Data
US 2003/0013658 A1    Jan. 16, 2003

Related U.S. Application Data

(62) Division of application No. 09/190,043, filed on Nov. 10, 1998, now Pat. No. 6,391,856.

(60) Provisional application No. 60/065,336, filed on Nov. 13, 1997.

(51) Int. Cl.
*A61K 38/00* (2006.01)
*A61K 38/07* (2006.01)
*C07K 7/00* (2006.01)
*C07K 5/103* (2006.01)

(52) U.S. Cl. .................. 514/12.2; 514/21.9; 530/330

(58) Field of Classification Search .................... 514/18; 530/330
See application file for complete search history.

(56) References Cited

OTHER PUBLICATIONS

Kermode et al. Biochem. J., vol. 276, pp. 715-723, 1991.*
Schubert C et al. Database Medline, AN 90120676; Archives of dermatological research, (1989) 281 (7) 475-81.*
Gleisner et al. Inflammation, 5, 13-17, 1981.*
References were furnished to applicant in the course of prosecution of parent case, U.S. Appl. No. 09/189,130.*
Bochner B Database Medline, AN 91086624; Journal of allergy and clinical immunology, (Dec. 1990) 86 (6 Pt 1) 830-9.*

* cited by examiner

*Primary Examiner* — Michael Borin
(74) *Attorney, Agent, or Firm* — Lathrop & Gage LLP

(57) ABSTRACT

Methods for treating cutaneous inflammation are described. Also described is a method for blocking IgE activation of a lymphocyte, a method for stabilizing the cell membrane of a lymphocyte, thereby preventing their further involvement in the increased inflammatory response to an IgE antigen challenge, and a method for inhibiting the migration of T-cells. Such methods involve administering to said patient a therapeutically effective amount of a peptide having the formula f-Met-Leu-X, wherein X is selected from the group consisting of Tyr, Tyr-Phe, Phe-Phe and Phe-Tyr.

3 Claims, 18 Drawing Sheets

ARACHIDONIC ACID METABOLISM

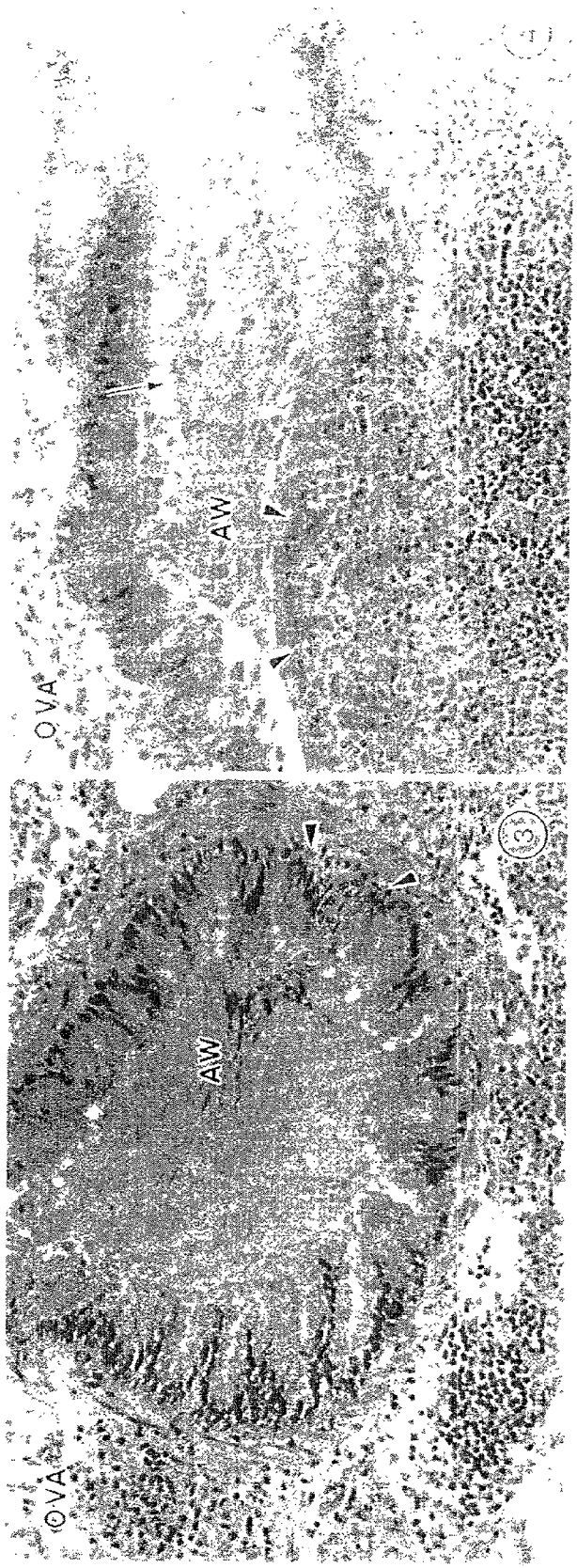

SEQUENCE LISTING (1) GENERAL INFORMATION:

(iii) NUMBER OF SEQUENCES: 5

(2) INFORMATION FOR SEQ ID NO: 1:

(i) SEQUENCE CHARACTERISTICS:
      (A) LENGTH: 4 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Modified-site
      (B) LOCATION:1
      (D) OTHER INFORMATION:/note= "The N-terminal amino acid is
         formylated."

(xi) SEQUENCE DESCRIPTION: SEQ ID NO: 1:

Met Leu Tyr Phe
1

(2) INFORMATION FOR SEQ ID NO: 2:

(i) SEQUENCE CHARACTERISTICS:
      (A) LENGTH: 4 amino acids
      (B) TYPE: amino acid
      (C) STRANDEDNESS: single

```
        (D) TOPOLOGY: linear (ii) MOLECULE TYPE: peptide (ix) FEATURE:
        (A) NAME/KEY: Modified-site
        (B) LOCATION:1
        (D) OTHER INFORMATION:/note= "The N-terminal amino acid
            is formylated."

(xi) SEQUENCE DESCRIPTION: SEQ ID NO: 2:

Met Leu Phe Phe
1

(2) INFORMATION FOR SEQ ID NO: 3:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:1
        (D) OTHER INFORMATION:/note= "The N-terminal amino acid
            is formylated."

(xi) SEQUENCE DESCRIPTION: SEQ ID NO: 3:

Met Leu Phe Tyr
1

(2) INFORMATION FOR SEQ ID NO: 4:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:1
        (D) OTHER INFORMATION:/note= "The N-terminal amino acid
            is formylated."

(xi) SEQUENCE DESCRIPTION: SEQ ID NO: 4:

Met Leu Phe Lys
1

(2) INFORMATION FOR SEQ ID NO: 5:

(i) SEQUENCE CHARACTERISTICS:
        (A) LENGTH: 4 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION:1
        (D) OTHER INFORMATION:/note= "The N-terminal amino acid
            is formylated."
```

(xi) SEQUENCE DESCRIPTION: SEQ ID NO: 5:

Met Leu Tyr Tyr
1

SMALL PEPTIDES AND METHODS FOR TREATMENT OF INFLAMMATION

This application is a divisional application of U.S. Ser. No. 09/190,043, filed Nov. 10, 1998, now U.S. Pat. No. 6,391,856, which claims the benefit of U.S. Provisional Application No. 60/065,366, filed Nov. 13, 1997.

FIELD OF THE INVENTION

This invention relates to small peptides having mast cell degranulation inhibition activity and to methods for treating inflammation, and particularly to N-formyl-methionyl peptides useful for the treatment of allergies such as allergic rhinitis, uticaria, anaphylaxis, drug sensitivity, food sensitivity, and the like, cutaneous inflammation such as dermatitis, eczema, psoraisis, contact dermatitis, sunburn, aging, and the like, and arthritis such as osteoarthritis, psoriatic arthritis, lupus, spondylarthritis, and the like. These peptides also are useful for treating chronic obstruction pulmonary disease and chronic inflammatory bowel disease. More particularly, the peptides can be used to replace corticosteroids in any application in which corticosteroids are used including immunosuppression in transplants and cancer therapy.

BACKGROUND OF THE INVENTION

Asthma is a complex disorder. Both hereditary and environmental factors—allergies, viral infections, irritants—are involved in the onset of asthma and in its inflammatory exacerbations. More than half of asthmatics (adults and children) have allergies; indeed, allergy to house dust mite feces is a major factor in the development of the disease and in the occurrence of exacerbations. Infection with respiratory syncytial virus during infancy is also highly associated with the development of asthma, and viral respiratory infections often trigger acute episodes.

The introduction three decades ago of bronchodilating beta$_2$-agonists—adrenergic agonists selective for the beta$_2$ receptor—revolutionized the treatment of asthma. These agents proved to be more potent and longer acting (4-6 hours) than the nonselective adrenergic receptor agonists such as isoproterenol, which stimulate both alpha- and beta-adrenergic receptors. Beta$_2$-agonists give rapid symptomatic relief and also protect against acute bronchoconstriction caused by stimili such as exercise or the inhalation of frigid air. Frequency of use can also serve as an indicator of asthma control. Recently, an extra long-acting beta$_2$-agonist-salmeterol (duration up to 12 hours) was introduced in the United States. Salmeterol is so potent that it may mask inflammatory signs; therefore, it should be used with an anti-inflammatory.

Theophylline is a relatively weak bronchodilator with a narrow therapeutic margin (blood level monitoring is recommended to avoid toxicity) and a propensity for drug interactions (competition for hepatic cytochrome P450 drug-metabolizing enzymes alters plasma levels of several important drugs metabolized by that same system).

Moderate asthma is treated with a daily inhaled anti-inflammatory-corticosteroid or mast cell inhibitor (cromolyn sodium or nedocromil) plus an inhaled beta$_2$-agonist as needed (3-4 times per day) to relieve breakthrough symptoms or allergen- or exercise-induced asthma. Cromolyn sodium and nedocromil block bronchospasm and inflammation, but are usually effective only for asthma that is associated with allergens or exercise and then, typically, only for juvenile asthmatics. Inhaled corticosteroids improve inflammation, airways hyperreactivity, and obstruction, and reduce the number of acute exacerbations. However, it takes a month before effects are apparent and up to a year for marked improvement to occur. The most frequent side effects are hoarseness and oral candidiasis. More serious side effects have been reported—partial adrenal suppression, growth inhibition, and reduced bone formation—but only with the use of higher doses. Beclomethasone, triamcinolone, and flunisolide probably have a similar mg-for-mg potency; the newer approvals budesonide and fluticasone are more potent and reportedly have fewer systemic side effects.

Even patients with mild disease show airways inflammation, including infiltration of the mucosa and epithelium with activated T cells, mast cells, and eosinophils. T cells and mast cells release cytokines that promote eosinophil growth and maturation and the production of IgE antibodies, and these, in turn, increase microvascular permeability, disrupt the epithelium, and stimulate neural reflexes and mucus-secreting glands. The result is airways hyperreactivity, bronchoconstriction, and hypersecretion, manifested by wheezing, coughing, and dyspnea.

Traditionally, asthma has been treated with oral and inhaled bronchodilators. These agents help the symptoms of asthma, but do nothing for the underlying inflammation. Recognition during the last 10 years of the importance of inflammation in the etiology of asthma has led to the increased use of corticosteroids, but many patients continue to suffer from uncontrolled asthma.

Scientists have determined that the leukotrienes (of which there are A, B, C, D, and E subtypes) plays a crucial role in asthma. They cause airways smooth muscle spasm, increased vascular permeability, edema, enhanced mucus production, reduced mucociliary transport, and leukocyte chemotaxis.

Like related prostaglandin compounds, leukotrienes are synthesized from arachidonic acid in the cell membrane. Arachidonic acid in mast cells, eosinophils, macrophages, monocytes, and basophils is formed from membrane phospholipids by the activation of phospholipase A2. After its formation, arachidonic acid undergoes metabolism via two major pathways: the cyclooxygenase pathway (which produced various prostaglandins and thromboxanes) and the 5-lipoxygenase pathway (which produces leukotrienes). A schematic of arachidonic acid metabolism is illustrated in FIG. 4. The prostaglandins, thromboxanes, and leukotrienes are known collectively as eicosanoids.

Anti-leukotrienes are members of a heterogeneous class of anti-asthma agents with the potential to interfere with the initial steps in the inflammatory cascade. Leukotrienes are inflammatory substances related to prostaglandins; both are generated from arachidonic acid in cell membranes. After arachidonic acid in mast cells, eosinophils, macrophages, monocytes, and basophils is formed, it is metabolized via two major pathways: (1) a cycloxygenase pathway (which produces prostaglandins and thromboxanes) and (2) the 5-lipoxygenase pathway, which produces leukotrienes in the cytoplasma. The leukotrienes are well known in medical science as the slow reacting substance of anaphylaxis ("SRS-A"). Leukotrienes play an important role in bronchial inflammation. They induce migration, adhesion and aggregation of various white blood cells (e.g., neutrophils, eosinophils, and monocytes) to blood vessels, increase capillary permeability, and cause bronchial and vessel smooth muscle constriction. The results include interstitial edema, leukocyte chemotaxis, mucus production, mucociliary dysfunction, and bronchospasm in the lungs. Certain classes of leukotrienes, for example, the cysteinyl leukotrienes (LTD$_4$), are particularly potent bronchoconstrictors, being approximately 100 to 1,000 times more active than histamine. Leukotrienes, including cysteinyl leukotrienes, are released from mast cells during degranulation.

A number of anti-leukotrienes that either block leukotriene receptors or prevent leukotriene synthesis by blocking the enzyme 5-lipoxygenase are under investigation and in commercial use. The leukotriene inhibitors are heterogeneous in action: some block 5-lipoxygenase directly, some inhibit the protein activating 5-lipoxygenase, and some displace arachidonate from its binding site on the protein. The leukotriene antagonists, by contrast, block the receptors themselves that mediate airways hyperactivity, bronchoconstriction, and hypersecretion.

Human lung mast cells produce tumor necrosis factor (TNF), IL-4 and IL-5 after IgE stimulation in vitro (*Chest* 1997; 112:523-29). Immunohistochemical analysis in endobronchial biopsy specimens has confirmed this together with IL-6 production. Further, mast cell counts and TNF are statistically more significant in asthmatics when compared to normal subjects. TNF and IL-4 can potentiate up-regulation of the expression of vascular cell adhesion molecule-1 (VCAM-1)—an adhesion molecule of the immunoglobin super family—in the endothelial layer of the bronchial vasculature. Eosinophils, basophils and mononuclear cells display the very late activation antigen 4 (VLA-4) integrin on their cellular surfaces, which interacts with VCAM-1. Thus, through the interaction VLA-4/VCAM-1, TNF and IL-4 facilitate the recruitment of circulating leukocytes. The capacity of mast cells to release preformed cytokines (TNF) on IgE-mediated stimulus or to rapidly synthesize others (IL-4, IL-5) could be the initial event leading to bronchial inflammation. In fact, the induction and activation of TH2 clones, through a further production of cytokines, facilitates the activation and recruitment of the eosinophils, which act as the terminal effectors of the inflammatory reaction. In turn, the cytokines produced by leukocytes (TH2 cells, in particular) profoundly affect the development, activation, and priming of mucosal mast cells, thus promoting a positive proinflammatory loop. The recent findings that human mast cells produce IL-8 and that murine pulmonary-derived mast cells express both chemokines, monocyte chemoattractant protein-1 and macrophage inflammatory protein-1. This suggests that, besides the cytokines classically involved in leukocyte recruitment (IL-4, IL-5, TNF), mast cells also elaborate additional, potent chemoattractants in the airways, acting on eosinophils and polymorphonuclear leukocytes (IL-8). Moreover, because chemokines acting as histamine-releasing factors elicit mast cell degranulation, they may further sustain an autocrine activating loop.

The mast cells also play a key role in B-cell growth to provide the cell contact (like basophils) that is required, along with IL-4, for IgE synthesis in vitro, which suggests that mast cells may directly regulate the production of IgE independently of T-cells, and may, upon IgE cross-linking, generate a sufficient amount of IL-4 to initiate a local TH2 response, the subset of T-cells considered to play a central role in atopic asthma. Moreover, mast cells can also act as an antigen-presenting cell to T-lymphocytes, suggesting an even larger role for mast cells in the immune network of asthma.

Inhibition of mast cell degranulation by N-formyl-methionyl-leucyl-phenylalanine was reported in *Inflammation*, Vol. 5, No. 1, pp. 13-16 (1981). There, it was reported that two structurally different chemotactic peptides, i.e., pepstatin and N-formyl-methionyl-leucyl-phenylalanine, inhibit the increase in vascular permeability produced by intradermal injection of 40/80, anti-rat IgE serum, or macromolecular anionic permeability factor isolated from calf lung in rat skin. It also has been reported that these peptides appear to act directly on the mast cells.

Because of the importance of treating inflammatory diseases in humans, particularly, for example, asthma, arthritis and anaphylaxis, new bioactive compounds having fewer side effects are continually being sought. The inhibition of mast cell degranulation by the intervention of novel peptides of the present invention within the context of the asthma inflammatory process is visually depicted in FIG. 4.

SUMMARY OF THE INVENTION

The present invention provides methods for treating a variety of indications using novel pharmaceutical compositions containing in a suitable pharmacological carrier a N-formyl-methionyl-leucyl ("f-Met-Leu") peptide having mast cell degranulation inhibition activity.

Particularly useful such peptides are those having the formula f-Met-Leu-X where X (SEQ ID NOs: 1, 2, and 3) is selected from the group consisting of Tyr, Tyr-Phe (SEQ ID NO: 1), Phe-Phe (SEQ ID NO; 2) and Phe-Tyr (SEQ ID NO: 3). Such peptides are useful for treating allergies such as allergic rhinitis, uticaria, anaphylaxis, drug sensitivity, food sensitivity, etc. and the like, cutaneous inflammation such as dermatitis, eczema, psoraisis, contact dermatitis, sunburn, aging, etc. and the like, and arthritis such as osteoarthritis, psoriatic arthritis, lupus, spondylarthritis, etc. and the like. These peptides also are useful for treating chronic obstruction pulmonary disease and chronic inflammatory bowel disease. The peptides of the present invention can be used to replace corticosteroids in any application in which corticosteroids are used including immunosuppression in transplants and cancer therapy.

In accord with the present invention, a method for treating an allergy reaction in a mammal comprises administering to the mammal an anti-allergic effective amount of a peptide having the formula f-Met-Leu-X where X (SEQ ID NOs: 1, 2, and 3) is selected from the group consisting of Tyr, Tyr-Phe (SEQ ID NO: 1), Phe-Phe (SEQ ID NO: 2) and Phe-Tyr (SEQ ID NO: 3). For treating allergies connected e.g. with nasal membranes, a preferred mode of administration is by inhalation. For treating contact allergies, a preferred mode of administration is topical application using a suitable pharmacological carrier. Intradermal injection or tablets can be used for systemic treatments.

The present invention also provides a method for treating cutaneous inflammation in a mammal.

The method comprises administering to the mammal an anti-inflammatory effective amount of a peptide having the formula f-Met-Leu-X where X (SEQ ID NOs: 1, 2, and 3) is selected from the group consisting of Tyr, Tyr-Phe (SEQ ID NO: 1), Phe-Phe (SEQ ID NO: 2) and Phe-Tyr (SEQ ID NO: 3).

The present invention further provides a method for treating arthritis selected from the group consisting of osteoarthritis, psoriatic arthritis, lupus, spondylarthritis, and the like in a mammal.

The method comprises administering to the mammal an anti-arthritic effective amount of a peptide having the formula f-Met-Leu-X where X (SEQ ID NOs: 1, 2, and 3) is selected from the group consisting of Tyr, Tyr-Phe (SEQ ID NO: 1), Phe-Phe (SEQ ID NO: 2) and Phe-Tyr (SEQ ID NO: 3).

In accord with another embodiment, the invention provides a method for inhibiting the infiltration of eosinophils into airways of a patient.

The method comprises administering to said patient an airway eosinophil infiltration inhibiting effective amount of a peptide having the formula f-Met-Leu-X, wherein X (SEQ ID NOs: 1, 2, and 3) is selected from the group consisting of Tyr, Tyr-Phe (SEQ ID NO: 1), Phe-Phe (SEQ ID NO: 2) and Phe-Tyr (SEQ ID NO: 3).

In accord with a further embodiment, the invention provides a method for inhibiting mucous release in airways in a patient.

The method comprises administering to the patient an airway mucous release inhibiting effective amount of a peptide having the formula f-Met-Leu-X where X SEQ ID NOs: 1, 2, and 3) is selected from the group consisting of Tyr, Tyr-Phe (SEQ ID NO: 1), Phe-Phe (SEQ ID NO: 2) and Phe-Tyr (SEQ ID NO: 3).

Also, the invention provides a method for treating chronic obstruction pulmonary disease in a patient.

The method comprises administering to the patient a chronic inflammatory bowel disease treatment effective amount of a peptide having the formula f-Met-Leu-X where X (SEQ ID NOs: 1, 2, and 3) is selected from the group consisting of Tyr, Tyr-Phe (SEQ ID NO: 1), Phe-Phe (SEQ ID NO: 2) and Phe-Tyr (SEQ ID NO: 3).

In addition, the present invention provides a method for treating chronic inflammatory bowel disease in a patient.

The method comprises administering to the patient a chronic inflammatory bowel disease treatment effective amount of a peptide having the formula f-Met-Leu-X where X (SEQ ID NOs: 1, 2, and 3) is selected from the group consisting of Tyr, Tyr-Phe (SEQ ID NO: 1), Phe-Phe (SEQ ID NO: 2) and Phe-Tyr (SEQ ID NO: 3).

The invention further provides a method for blocking IgE activation of lymphocytes such as, for example, macrophages, monocytes, eosinophils, neutrophils, TNF and the like.

The method comprises contacting said lymphocytes with an IgE activation blocking effective amount of a peptide having the formula f-Met-Leu-X where X (SEQ ID NOs: 1, 2, and 3) is selected from the group consisting of Tyr, Tyr-Phe (SEQ ID NO: 1), Phe-Phe (SEQ ID NO: 2) and Phe-Tyr (SEQ ID NO: 3).

The invention also provides a method for stabilizing the cell membrane of lymphocytes such as, for example, macrophages, monocytes, eosinophils, neutrophils, TNF, and the like, thereby preventing their further involvement in the increased inflammatory response to an IgE antigen challenge.

The method comprises contacting said lymphocytes with an cell stabilization effective amount of a peptide having the formula f-Met-Leu-X where X (SEQ ID NOs: 1, 2, and 3) is selected from the group consisting of Tyr, Tyr-Phe (SEQ ID NO: 1), Phe-Phe (SEQ ID NO: 2) and Phe-Tyr (SEQ ID NO: 3).

Further, the invention also provides a method for inhibiting the migration of T-cells such as, for instance, $CD4^+$ cells, thereby preventing their involvement in the production of IL-4 and IL-5, as well as other chemokines.

The method comprises contacting said T-cells with a T-cell migration inhibiting effective amount of a peptide having the formula f-Met-Leu-X where X (SEQ ID NOs: 1, 2 and 3) is selected from the group consisting of Tyr, Tyr-Phe (SEQ ID NO: 1), Phe-Phe (SEQ ID NO: 2) and Phe-Tyr (SEQ ID NO: 3).

In certain preferred embodiments of the present invention, patients can benefit by administering the peptide of the present invention in combination with a second active ingredient. Particularly useful other active ingredients for such combination in accord with the present invention are, for example, antileukotrienes, $beta_2$ agonists, corticosteroids, and the like.

BRIEF DESCRIPTION OF DRAWINGS

FIGS. 9A-9D show the histopathology of lung tissues of a second group of mice treated in accord with the present invention after induced with asthma.

DETAILED DESCRIPTION OF THE INVENTION

Figure 1:
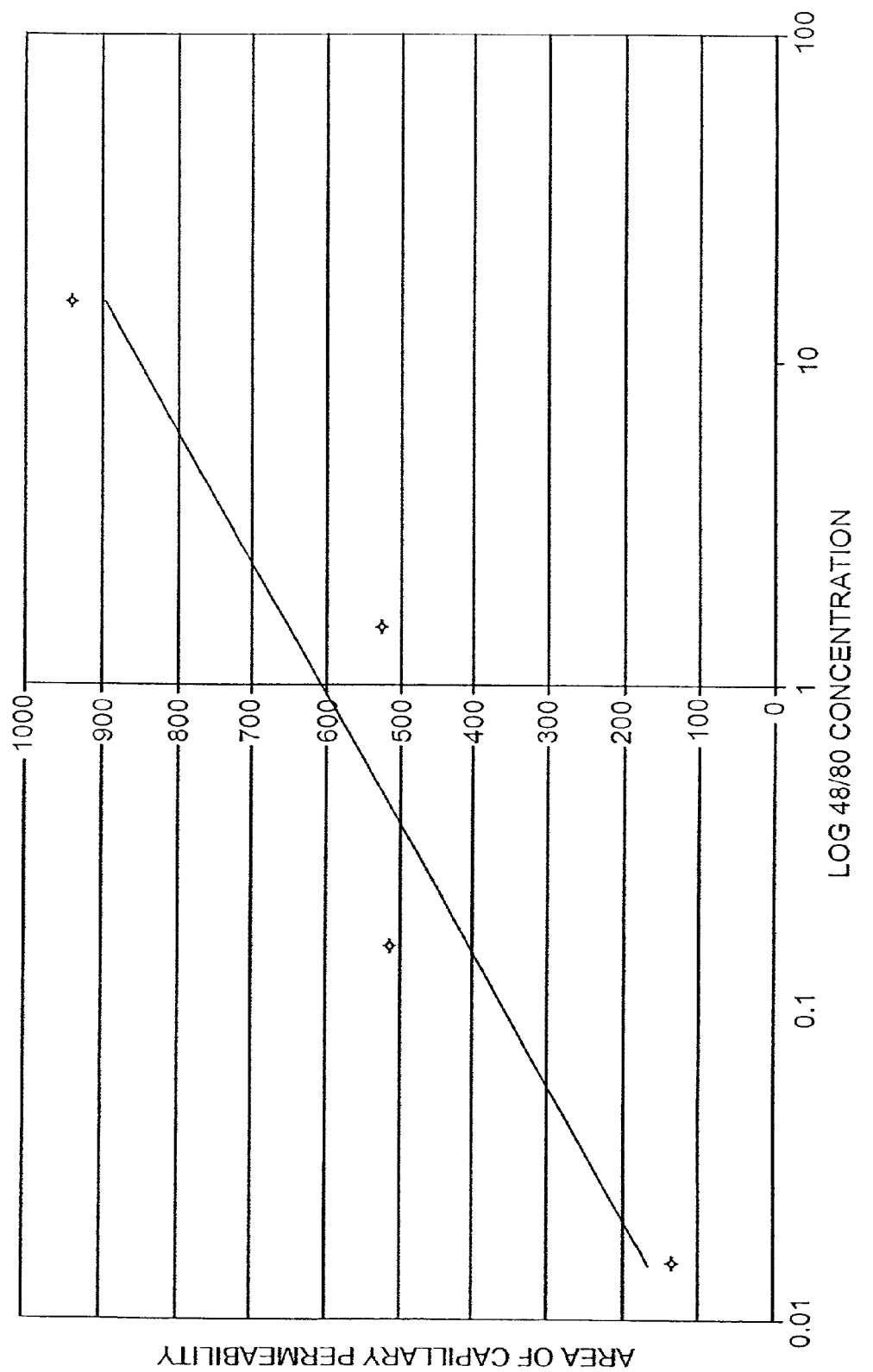
FIG. 1 is a log dose response curve illustrating area of capillary permeability for various concentrations of Compound 48/80.

In accord with the present invention, certain small peptides having the formula f-Met-Leu-X where X (SEQ ID NOs: 1, 2 and 3) is selected from the group consisting of Tyr, Tyr-Phe (SEQ ID NO: 1), Phe-Phe (SEQ ID NO: 2) and Phe-Tyr (SEQ ID NO: 3) have been found to have surprising activity for inhibiting the degranulation of mast cells. As a result, such peptides inhibit the release of cytokines (such as, for example, TNF), as well as histamines and leukotrienes and they are useful for treatment of inflammation, which can result from a variety of ailments such as, for example, asthma, allergies such as allergic rhinitis, uticaria, anaphylaxis, drug sensitivity, food sensitivity, etc. and the like, cutaneous inflammation such as dermatitis, eczema, psoraisis, contact dermatitis, sunburn, aging, etc. and the like, and arthritis such as osteoarthritis, psoriatic arthritis, lupus, spondylarthritis, etc. and the like. These peptides also are useful for treating chronic obstruction pulmonary disease and chronic inflammatory bowel disease. The peptides of the present invention can be used to replace corticosteroids in any application in which corticosteroids are used including immunosuppression in transplants and cancer therapy.

Continued mast cell degranulation and its release of leukotrienes, histamines, and other cytokines decreases, or ceases entirely in preferred embodiments, following treatment with peptides of the present invention. In accord with preferred embodiments of the present invention, the peptides also can reduce the infiltration of eosinophils, basophils and neutrophils into inflammatory tissues. Lymphocytes, eosinophils, and neutrophils do not exhibit chemotaxis in response to preferred peptides of the present invention. As a consequence, the chemotactic adhesion, migration and aggregation of lymphocytes, eosinophils and neutrophils to the site of inflammation is significantly reduced, as is vascular permeability at the inflammation site. Further, preferred compounds of the present invention exhibit no toxicity to vital organs such as heart, liver and lungs.

Preferred peptides, in accord with the present invention, provide a receptor link that blocks IgE activation of lymphocytes such as, for example, macrophages, monocytes, eosinophils, neutrophils, TNF, and the like, in vitro and in vivo. The peptides stabilize the cell membrane of such lymphocytes, preventing their further involvement in the increased inflammatory response to an IgE antigen challenge. The peptides also block cross-cell IgE linking in chronic inflammation, for example, between mast cells and eosinophils.

The peptides of this invention can be prepared by conventional small peptide chemistry techniques. The peptides when used for administration are prepared under aseptic conditions with a pharmaceutically acceptable carrier or diluent.

Doses of the pharmaceutical compositions will vary depending upon the subject and upon the particular route of administration used. Dosages can range from 0.1 to 100,000 μg/kg a day, more preferably 1 to 10,000 μg/kg. Most preferred dosages range from about 1 to 100 μg/kg of body weight, more preferably from about 1 to 10 μg/kg and most preferably 1.0 to 2.0 μg/kg. Doses are typically administered from once a day to every 4-6 hours depending on the severity of the condition. For acute conditions, it is preferred to administer the peptide every 4-6 hours. For maintenance or therapeutic use, it may be preferred to administer only once or twice a day. Preferably, from about 0.18 to about 16 mg of peptide are administered per day, depending upon the route of administration and the severity of the condition. Desired time intervals for delivery of multiple doses of a particular composition can be determined by one of ordinary skill in the art employing no more than routine experimentation.

Routes of administration include oral, parenteral, rectal, intravaginal, topical, nasal, ophthalmic, direct injection, etc. In a preferred embodiment, the peptides of this invention are administered to the patient in an anti-inflammatory effective amount or in a dosage that inhibits degranulation of mast cells. An exemplary pharmaceutical composition is a therapeutically effective amount of a peptide in accord with the present invention that provides anti-inflammatory effect or that inhibits degranulation of mast cells, typically included in a pharmaceutically acceptable carrier.

The term "pharmaceutically acceptable carrier" as used herein, and described more fully below, includes one or more compatible solid or liquid filler diluents or encapsulating substances that are suitable for administration to a human or other animal. In the present invention, the term "carrier" thus denotes an organic or inorganic ingredient, natural or synthetic, with which the molecules of the invention are combined to facilitate application. The term "therapeutically-effective amount" is that amount of the present pharmaceutical compositions, which produces a desired result or exerts a desired influence on the particular condition being treated. Various concentrations may be used in preparing compositions incorporating the same ingredient to provide for variations in the age of the patient to be treated, the severity of the condition, the duration of the treatment and the mode of administration.

The carrier must also be compatible. The term "compatible", as used herein, means that the components of the pharmaceutical compositions are capable of being commingled with a small peptides of the present invention, and with each other, in a manner such that does not substantially impair the desired pharmaceutical efficacy.

The small peptides of the invention are typically administered per se (neat). However, they may be administered in the form of a pharmaceutically acceptable salt. Such pharmaceutically acceptable salts include, but are not limited to, those prepared from the following acids: hydrochloric, hydrobromic, sulfuric, nitric, phosphoric, maleic, acetic, salicylic, p-toluene-sulfonic, tartaric, citric, methanesulphonic, formic, malonic, succinic, naphthalene-2-sulfonic, and benzenesulphonic. Also, pharmaceutically acceptable salts can be prepared as alkaline metal or alkaline earth salts, such as sodium, potassium or calcium salts of the carboxylic acid group. Thus, the present invention provides pharmaceutical compositions, for medical use, which comprise peptides of the invention together with one or more pharmaceutically acceptable carriers thereof and optionally any other therapeutic ingredients.

The compositions include those suitable for oral, rectal, intravaginal, topical, nasal, ophthalmic or parenteral administration, all of which may be used as routes of administration using the materials of the present invention. Pharmaceutical compositions containing peptides of the present invention may also contain one or more pharmaceutically acceptable carriers, which may include excipients such as stabilizers (to promote long term storage), emulsifiers, binding agents, thickening agents, salts, preservatives, solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the peptide of this invention, its use in pharmaceutical preparations is contemplated herein. Supplementary active ingredients can also be incorporated into the compositions of the present invention.

Compositions suitable for oral administration are preferred for treatment of asthma. Typically, such compositions are prepared as an inhalation aerosol, nebule, syrup or tablet. Compositions suitable for topical administration are preferred for treatment of arthritis, although oral compositions also can be convenient. Typically, such topical compositions are prepared as a cream, an ointment, or a solution. The concentrations of the peptide active ingredient in such compositions is typically less than 50 μg/ml, more preferable less than 30 μg/ml, and most preferably from about 5 to 10 μg/ml.

The compositions may conveniently be presented in unit dosage form and may be prepared by any of the methods well known in the art of pharmacy. Methods typically include the step of bringing the active ingredients of the invention into association with a carrier that constitutes one or more accessory ingredients.

Compositions of the present invention suitable for inhalation administration may be presented, for example, as aerosols or inhalation solutions. An example of a typical aerosol composition consists of the desired quantity of microcrystalline peptide suspended in a mixture of trichloromonofluoromethane and dichlorodifluoromethane plus oleic acid. An example of a typical solution consists of the desired quantity of peptide dissolved or suspended in sterile saline (optionally about 5% v/v dimethylsulfoxide ("DMSO") for solubility), benzalkonium chloride, and sulfuric acid (to adjust pH).

Compositions of the present invention suitable for oral administration also may be presented as discrete units such as capsules, cachets, tablets or lozenges, each containing a predetermined amount of the peptide of the invention, or which may be contained in liposomes or as a suspension in an aqueous liquor or non-aqueous liquid such as a syrup, an elixir, or an emulsion. An example of a tablet formulation base includes corn starch, lactose and magnesium stearate as inactive ingredients. An example of a syrup formulation base includes citric acid, coloring dye, flavoring agent, hydroxypropylmethylcellulose, saccharin, sodium benzoate, sodium citrate and purified water.

Compositions suitable for parenteral administration conveniently comprise a sterile aqueous preparation of the molecule of the invention, which is preferably isotonic with the blood of the recipient. This aqueous preparation may be formulated according to known methods using those suitable dispersing or vetting agents and suspending agents. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In aqueous solutions, up to about 10% v/v DMSO or Trappsol can be used to maintain solubility of some peptides. Also, sterile, fixed oils may be conventionally employed as a solvent or suspending medium. For this purpose, a number of fixed oils can be employed including synthetic mono- or diglycerides. In addition, fatty acids (such as oleic acid or neutral fatty acids) can be used in the preparation of injectibles. Further, Pluronic block copolymers can be formulated with lipids at 4° C. for compound injection on a time release basis from solid form at 37° C. over a period of weeks or months.

Compositions suitable for topical administration may be presented as a solution of the peptide in Trappsol or DMSO, or in a cream, ointment, or lotion. Typically, about 0.1 to about 2.5% active ingredient is incorporated into the base or carrier. An example of a cream formulation base includes purified water, petrolatum, benzyl alcohol, stearyl alcohol, propylene glycol, isopropyl myristate, polyoxyl 40 stearate, carbomer 934, sodium lauryl sulfate, acetate disodium, sodium hydroxide, and optionally DMSO. An example of an ointment formulation base includes white petrolatum and optionally mineral oil, sorbitan sesquioleate, and DMSO. An example of a lotion formulation base includes carbomer 940, propylene glycol, polysorbate 40, propylene glycol stearate, cholesterol and related sterols, isopropyl myristate, sorbitan palmitate, acetyl alcohol, triethanolamine, ascorbic acid, simethicone, and purified water.

The Rat Skin Model for Determination of Inhibition of Mast Cell Degranulation

Allergy induced asthma results from exposure of substances (allergens) to which an organism has become hypersensitized. Exposure to allergen results in degranulation of mast cells in the lung, releasing leukotrienes and histamines. In response to the release of leukotrienes and histamines, capillary permeability is dramatically increased and blood plasma leaks from the capillaries into the surrounding tissues. Respiratory symptoms resulting from such an exposure range from mild (itching and sneezing) to potentially fatal (asthma), including in extreme chronic cases death by anaphylaxis.

To demonstrate this phenomenon experimentally, rat skin is substituted for lung. In this model, the blood plasma of the experimental rat is labeled with the dye trypan blue. This soluble dye is carried in the bloodstream as a passive marker of plasma itself, and is excluded from live cells. Intact blood vessels, including the capillary system, retain this dye under normal circumstances. A compound, which induces degranulation of mast cells (resulting in leukotriene and histamine release), is injected into the skin to simulate allergen-induced degranulation. In these experiments, Compound 48/80 was used for this purpose. In the events following leukotriene and histamine release, capillary permeability is increased, and plasma, dyed blue, leaks from capillaries and dyes the skin surrounding the injection site blue. The area of bluing is a measure of the amount of Compound 48/80 injected.

A compound can be tested for "anti-leukotriene" and/or "anti-histamine" activity by mixing it with Compound 48/80 prior to injection. If the test compound inhibits leukotriene or histamine release, an area of bluing of smaller diameter is observed when compared to an injection site on the same rat into which Compound 48/80 has been injected without any of the test compound. In the case of high anti-leukotriene and anti-histamine activity, the bluing may actually be totally inhibited.

Experimental

The rat skin model was undertaken and validated. Various peptides were tested at a predetermined dose for anti-leukotriene and/or anti-histamine activity. The dose selected allowed a general comparison to f-Met-Leu-Phe, which was standard compound for comparison.

A "dose response" titration was performed for some compounds and compared with the standard compound. Observing serial decreases in the size areas of capillary permeability using serially smaller doses of the putative inhibitory compound validates the inhibition of leukotriene and/or histamine release observed in the initial predetermined dose test.

Materials and Methods

Reagents were obtained from Sigma or Aldrich, with the exception of ketamine, a veterinary anaesthetic that was obtained from various veterinary suppliers. The rats used were male Sprague-Dawley breed, 220-240 g at time of purchase from B&K International.

For the rat skin reaction, rats were anaesthetized with 0.25 ml 10 mg/ml ketamine. 1.0 ml trypan blue in saline (sterile filtered) was administered in a tail vein, and the back of the rat was shaved. Four intradermal injection sites per rat were used for test and control injections.

Compound 48/80 was prepared as a 1.5 mg/ml stock solution in saline. This material was found to be potentially unstable in aqueous solution and was prepared freshly each day. Serial dilutions in saline to working levels were prepared just prior to injection of each rat.

Peptides were prepared as a 23 mM stock solution in DMSO, and stored at −20° C. between experiments. At the time of use, the frozen stock solutions were thawed, and appropriate aliquots added to dilutions of Compound 48/80, along with appropriate amounts of DMSO, to result in the ratio of 5 µl DMSO to 0.1 ml aqueous Compound 48/80. This resulted in a 5% solution of DMSO, necessary to maintain solubility of certain peptides. The effect of 5% DMSO was demonstrated by control experiments to be nil.

For injections, 0.1 ml Compound 40/80, +/− test compounds were injected intradermally into anaesthetized, dyed, and shaved rats. Following a 15 minute incubation, the rats were sacrificed by cervical dislocation and the back skin was evulsed and placed on a light box. An image of the backlit skin was digitized using a CCD video capture camera and compatible hardware/software. The digitized image was analyzed using a scientific graphics analysis software package, and the areas of capillary permeability (bluing) were integrated and digital values were obtained for further analysis.

A dose response curve was generated using Compound 48/80 at various doses from ca. 0.01 µg through ca. 15 µg. The results are shown in FIG. 1. Wide variability was noted in the diameter of areas of capillary permeability for a given dose of Compound 48/80 based upon rat-to-rat variations (e.g., thickness of skin). A dose of 0.15 µg of Compound 48/80 was selected for conducting further tests.

EXAMPLE 1

Figure 2:
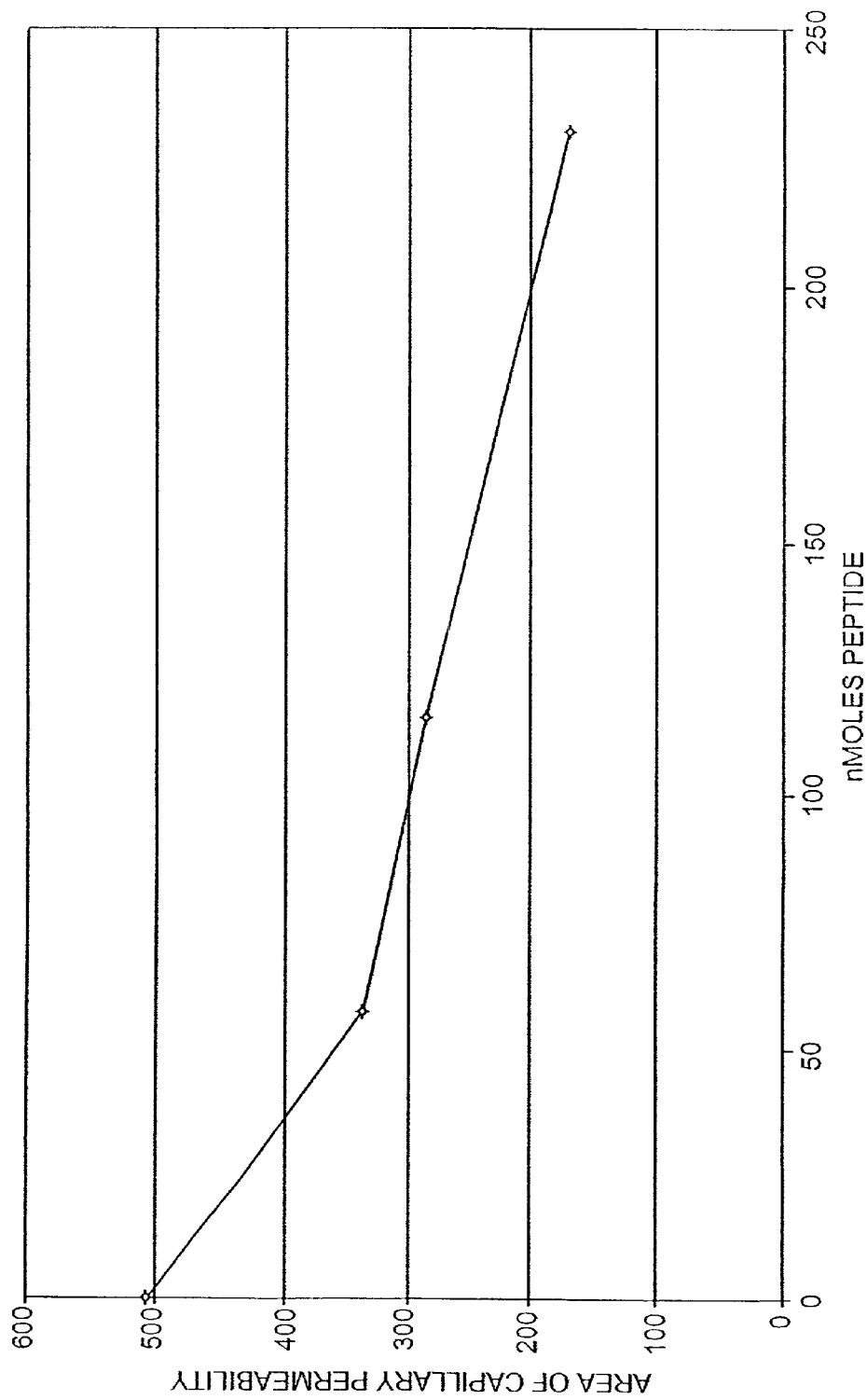
FIG. 2 is a dose response curve for inhibition of capillary permeability by various concentrations of f-Met-Leu-Phe.

A dose response curve was prepared for the standard compound, f-Met-Leu-Phe, using the selected dose of 0.15 µg Compound 48/80. Doses of 0 to about 230 nM of f-Met-Leu-Phe were tested and the results are shown in FIG. 2. Inhibition of degranulation induced by Compound 48/80 was clearly shown.

EXAMPLES 2-11

Several f-Met-Leu peptides were tested for inhibition of induced degranulation in the rat skin model using 100 nanomoles of the test peptide and a dose of 0.15 µg Compound 48/80. An intrinsic zero-peptide-dose 48/80 control was included in each rat for each experiment, and the % of inhibition was expressed in relative terms to this control (0% inhibition). The percent mast cell degranulation produced by 48/80 was also determined. The results are tabulated below.

TABLE 1

| Example | Peptide | % Inhibition | % Degranulation* |
|---|---|---|---|
| 2 | f-Met-Leu-Phe (prior art) | 30 | 60 |
| 3 | N-acetyl-Met-Leu-Phe | 0 | 98 |
| 4 | N-t-BOC-Met-Leu-Phe | 0 | — |
| 5 | f-Met-Leu-(iodo)Phe | 0 | — |
| 6 | f-Met-Leu-Phe(benzylamide) | 0 | — |
| 7 | f-Met-Leu-Phe-Lys (SEQ ID NO: 4) | 0 | — |
| 8 | f-Met-Leu-Phe(methyl ester) | 0 | — |
| 9 | f-Met-Leu-Phe-Phe (SEQ ID NO: 2) | 100 | 1-3 |
| 10 | f-Met-Leu-Tyr | 55 | 30 |
| 11 | f-Met-Leu-Tyr-Tyr (SEQ ID NO: 5) | 0 | — |

EXAMPLE 12

Figure 3:
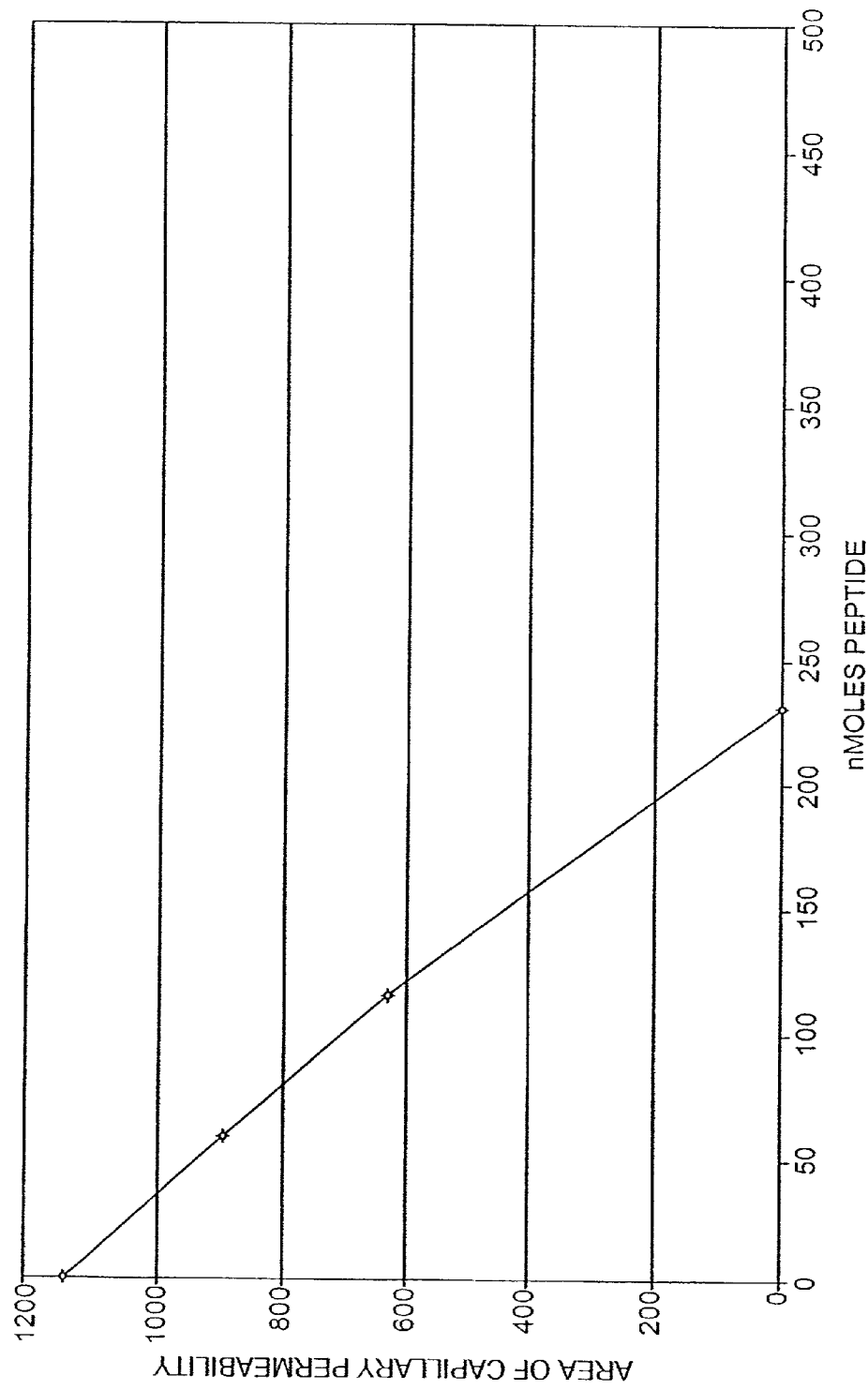
FIG. 3 is a dose response curve for inhibition of capillary permeability by various concentrations of a preferred peptide of the present invention.
Figure 4:
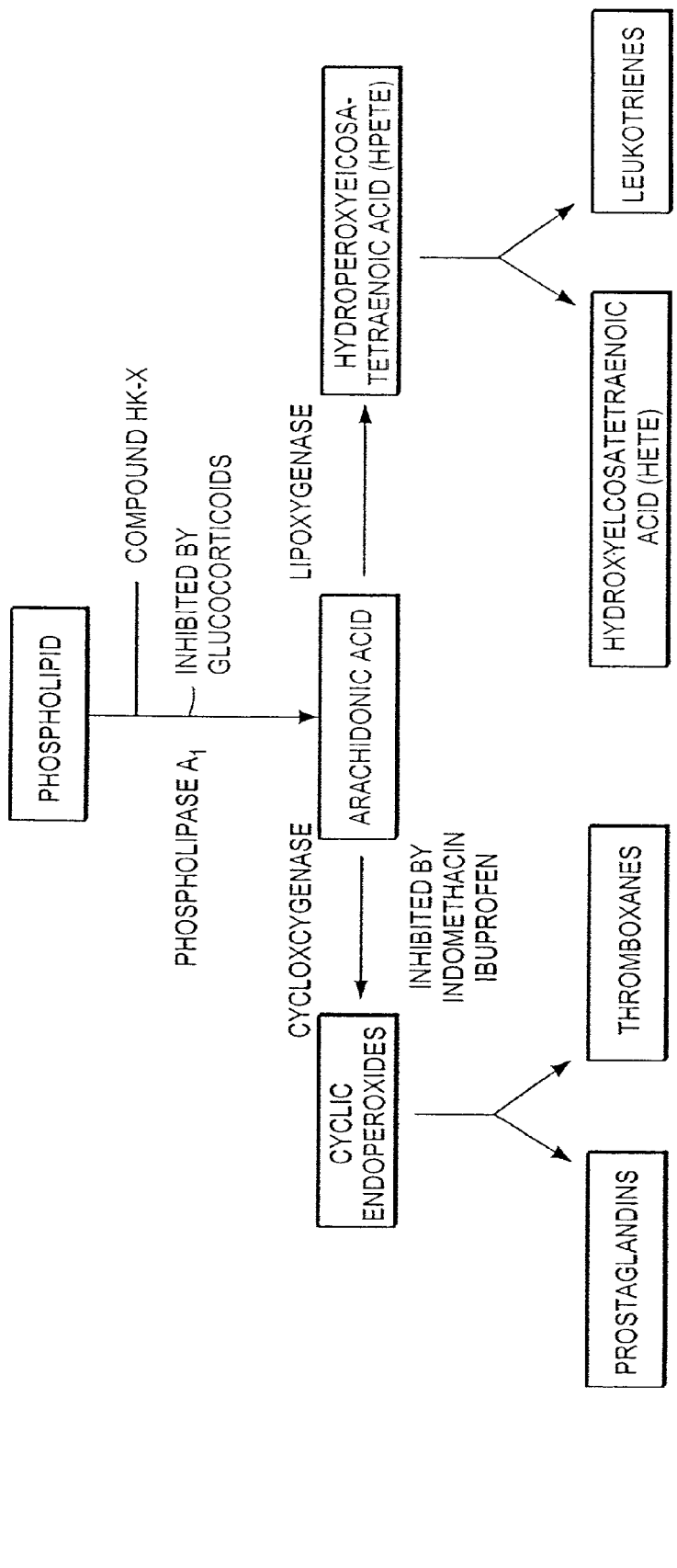
FIG. 4 is a schematic illustration of the major pathways for arachidonic acid metabolism further illustrating inhibition of mast cell degranulation.

A dose response curve was prepared for f-Met-Leu-Phe-Phe (SEQ ID NO:2) using the selected dose of 0.15 µg Compound 48/80. Doses of 0 to about 230 nM of f-Met-Leu-Phe-Phe (SEQ ID NO:2) were tested and the results are shown in FIG. 3. Surprisingly remarkable inhibition of degranulation induced by Compound 48/80 was clearly shown. The inhibition of induced degranulation for f-Met-Leu-Phe-Phe was unexpectedly substantially better than that of the standard compound f-Met-Leu-Phe.

The OVA-induced Bronchial Asthma Mouse Model for Inhibition of Mast Cell Degranulation Asthma is a complex disease, which is characterized by spontaneous exacerbation of airways obstruction and persistent bronchial hyperresponsiveness. Chronic infiltration with activated T-lymphocytes, eosinophils and macrophages/monocytes of the airway submucosa is another established feature. Inflammatory mechanisms, with expression of cytokines, and the release of inflammatory mediators, underlie the pathogenesis of bronchoconstriction and bronchial hyperresponsiveness. However, much of the pathogenic mechanism remains unclear, e.g., the mechanisms that induce persistence of symptoms and chronic inflammation and the interventions necessary to control and prevent the disease.

It has long been recognized that a single inhaled allergen challenge can induce an acute increase in airway responsiveness in some individuals and animal models. However, repeated allergen inhalations have demonstrated more pronounced, consistent, and prolonged increases in airway responsiveness. This mouse model of long-term repeated inhalations of allergen has been used to study the long term effect of allergic diseases in the lung, and to delineate the cells, mechanisms, molecules, and mediators involved in the induction of airway hyperresponsiveness of lung in humans.

Materials and Methods

Reagents: Crystalline OVA was obtained from Pierce Chem. Co. (Rockford, Ill.) aluminum potassium sulfate (alum) from Sigma Chem. Co. (St. Louis, Mo.), pyrogen-free distilled water from Baxter, Healthcare Corporation (Deerfield, Ill.), 0.9% sodium chloride (normal saline) from Lymphomed (Deerfield, Ill.) and Trappsol™ HPB-L100 (aqueous hydroxypropyl beta cyclodextrin; 45 wt/vol % aqueous solution) from Cyclodextrin Technologies Development, Inc. (Gainesville, Fla.). The OVA (500 µg/ml in normal saline) was mixed with equal volumes of 10% (wt/vol) alum in distilled water. The mixture (pH 6.5 using 10 N NaOH) after incubation for 60 minutes at room temperature underwent centrifugation at 750 g for 5 minutes; the pellet was resuspended to the original volume in distilled water and used within one hour.

The selective 5-lipoxtgenase inhibitor, Zileuton (N-[1-benzo[b]thien-2-ylethyl]-N-hydroxyurea; *J. Pharmacol Exp Ther.* 1991; 256: 929-937), was kindly provided by Drs. Bell and George W. Carter (Abbott Laboratories, Abbott Part, Ill.). Zileuton was dissolved in Trappsol.™. Histatek, Inc. (Seattle, Wash.) provided the mast cell degranulation inhibitor, f-Met-Leu-Phe-Phe ("HK-X").

Female BALB/c Once (6-8 wk of age at purchase; D and K, Seattle Wash.) were housed under conventional conditions for the studies.

Figures 5A, 5B:
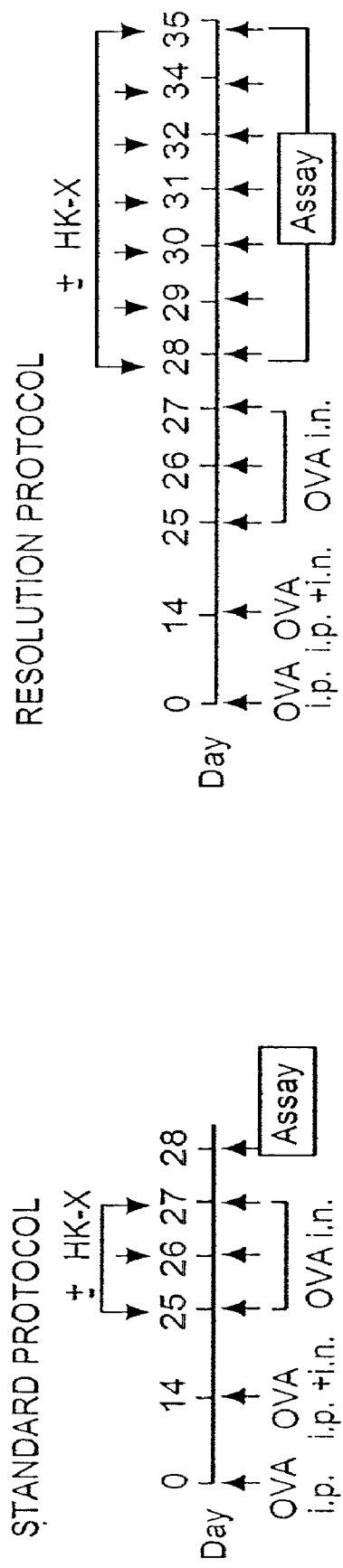
FIGS. 5A and -5B are schematic illustrations of the different protocols of Standard (5A) and Resolution (5B) used in The OVA-induced Bronchial Asthma Mouse Model.

Allergen Immunization/Challenge Protocols: Mice received an i.p. injection of 0.2 ml (100 µg) of OVA with alum on the different protocols of Standard (FIG. 5A) and Resolution (FIG. 5B) (*J. Exp Med.* 1996; 184: 1483-1494). According to the different protocols, mice were anesthetized with 0.2 ml i.p. of ketamine (0.44 mg/ml)/xylazine (6.3 mg/ml) in normal saline before receiving an intranasal (i.n.) does of 100 µg OVA in 0.05 ml normal saline and an i.n. dose of 50 µg OVA in 0.05 ml normal saline separately on different days. Two control groups were used. Accordingly, the first group received normal saline with alum i.p. and normal saline without alum i.n.; the second group received OVA with alum i.p., OVA without alum i.n., and normal saline, alone.

Histology

The trachea and left lung (the right lung is used for bronchoalveolar lavage ("BAL")) were obtained and fixed in 10% neutral formaldehyde solution at room temperature for 6~15 h. After being embedded in paraffin, the tissues were cut into 5-um sections and processed with the different staining or immunolabling further. Discombe's eosinophil staining was used for counting the cell numbers with the counterstain of methylene blue. The eosinophil number per unit airway area (2,200 µm$^2$) was determined by morphometry (*J. Pathol.* 1992; 166: 395-404; *Am Rev Respir Dis.* 1993; 147:448-456). Fibrosis was identified with the Masson's trichrome staining. Airway mucus was identified by the following staining method: methylene blue, hematoxylin and eosin, mucicarmine, alcian blue, and alcian blue/periodic acid-Schiff (PAS) reaction (Troyer, H., "Carbohydrates" in *Principles and Techniques of Histochemistry*, Little, Brown and Company, Boston, Mass., 1980: 89-121; Sheehan, D. C., et al., "Carbohydrates" in *Theory and Practice of Histotechnology*, Battle Press, Columbus, Ohio, 1980: 159-179) Mucin was stained with mucicarmine solution; metanil yellow counterstain was employed. Acidic mucin and sulfated mucosubstances were stained with alcian blue, pH 2.5; nuclear fast red counterstain was used. Neutral and acidic mucosubstances were identified by alcian blue, pH 2.5, and PAS reaction. The degree of mucus plugging of the airways (0.5-0.8 mm in diameter) was also assessed by morphometry. The percent occlusion of airway diameter by mucus was classified on a semiquantitative scale from 0 to 4+ as described in Figure Legends. The histologic and morphometric analyses were performed by individuals blinded to the protocol design.

Pulmonary Function Testing

On day 28, 24 hours after the last i.n. administration of either normal saline or OVA, pulmonary mechanics to intravenous infusion of methacholine were determined in mice in vivo by a plethysmographic method, which was modified from that previously described (10, 1958; 192: 364-368; *J. Appl. Physiol.* 1988; 64: 2318-2323; *J. Exp. Med.* 1996; 184: 1483-1494). At the completion of pulmonary function testing, each mouse was exsanguinaetd by cardiac puncture and the lung tissue with trachea was obtained for the further analysis.

Bronchoalveolar Lavage

After tying off the left lung at the mainstem bronchus, the right lung was lavaged three times with 0.4 ml of normal saline. Bronchoalveolar lavage (BAL) fluid cells from a 0.05-ml aliquot of the pooled sample were counted sing a hemocytometer and the remaining fluid centrifuged at 4° C. for 10 minutes at 200 g. The supernatant was stored at –70° C. until eicosanoid analysis was performed. After resuspension of the cell pellet in normal saline containing 10% bovine serum albumin ("BSA"), BAL cell smears were made on glass slides. To stain eosinophils, dried slides were stained with Discombe's diluting fluid (0.05% aqueous eosin and 5% acetone (vol/vol) in distilled water; *J. Exp. Med.* 1970; 131: 1271-1287) for 5-8 minutes, rinsed with water for 0.5 minutes, and counterstained with 0.07% methylene blue for 2 minutes.

Assay of Airway Mucus Glycoproteins

Mucus glycoproteins in BAL fluid were assayed by slot blotting and PAS staining (*Anal. Biochem.* 1989; 182: 160-164; *Am. J. Respir. Cell Mol. Biol.* 1995; 12: 296-306). Nitrocellulose membranes (0.2-µm pore size; Schleicher & Schuell, Keene, N.H.) were wetted in distilled water and then in normal saline before placement in a Minifold II 72-well slot blot apparatus (Schleicher & Schuell). The BAL fluid samples (0.05 ml) and aliquots (0.05-75 l) of a stock solution (2 µm/ml) of human respiratory mucin glycoprotein (*Am. J. Respir. Cell Mol. Biol.* 1991; 5: 71-79) were blotted onto the nitro-cellulose membranes by water suction vacuum, and mucus glycoproteins were visualized by PAS reaction. Reflectance densitometry was performed to quantitate the PAS staining. The images were than analyzed by an image processing system described below. The integrated intensity of the PAS reactivity of the BAL samples was quantitated by comparison to the standard curve for human respiratory mucin.

Immunocytochemistry

Monoclonal antibody: CD11c (DAB method) and Mac1 (Beringer Mannheim, ABC method with Hitomouse Kit, Zymed) were used to identified the inflammatory cell types, e.g., dendric cells, macrophages and lymphocytes, in/around the areas of vasculatures, airways and fibrosis.

Morphometry and Image Analysis

All the images were captured and digitized by a ScanJet IICX Scanner with HP DeskScan II software (Microsoft® Windows™ Version) (Hewlett Packard, Palo Alto, Calif.). This system was linked to Dell Dimension XPS P90 computer (Dell Corporation, Austin, Tex.) employing Image-Pro® Plus, version 1.1 for Windows™ software (Media Cybernetics, Silver Spring, Md.). The images were assessed on a 256 gray level scale using a Dell Ultrascan 17ES monitor with extra high-resolution graphics mode (1.280×1,024 pixels, 78.9-kHz horizontal scanning frequency, 74-Hz vertical scanning frequency).

Leukotriene Inhibitor Studies

To assess the role of 5-lipoxygenase products in airway inflammation, the 5-lipoxygenase inhibitor, Zileuton, (35 mg/kg) was given i.p. 30 minutes before each i.n. challenge on the days according to FIG. 5. In one set of animals, Zileuton was also given before i.p. OVA. Zileuton at 35 mg/kg inhibits cysteinyl leukotriene release by ~95% in passively sensitized rats given BSA antigen i.p. (*J. Pharmacol. Exp. Ther.* 1991; 256: 929-937).

Compound HK-X of the Invention

Compound HK-X was administered at 5 mg/kg and 10 mg/kg using the same procedure as described above.

Statistical Analyses

The pulmonary function data were evaluated by analysis of variance (ANOVA) using the protected least significant difference method (Statview II, Abacus Concepts, Berkeley, Calif.). This method uses a multiple t statistic to evaluate all possible pairwise comparisons and is applicable for both equal and unequal pair sizes. The other data are reported as the mean±SE of the combined experiments. Differences were analyzed for significance (P<0.05) by Student's two-tailed t test for independent means.

1. Eosinophils (TABLES 2A-2B)

The eosinophil numbers of the airway in OVA-treated mouse of 1-, 2- and 3-month group were significantly reduced from 44.83% to 37.40% and 19.15%, respectively (P<0.025). Even though the eosinophil count is much higher in the OVA treated group than the other two groups at the same time course (P<0.025), Zileuton could reduced eosinophils generally through 1-3 month. However, the HK-X compound of the present invention reduced eosinophils comparably at one month, but much more beneficially at two and three months.

TABLE 2A

AIRWAY INFLUX OF EOSINOPHILS

| (%) | Saline | OVA | Zileuton | HK | P value |
|---|---|---|---|---|---|
| 3 month | 1.00 | 19.15 | 10.73 | — | <0.025 |
| 2 month | 1.00 | 37.40 | 11.66 | — | <0.01 |
| 1 month | 1.00 | 44.83 | 15.50 | 14.20 | <0.001 |
| P value | >0.05 | <0.025 | <0.025 | <0.025 | |

TABLE 2B

PERCENTAGE OF EOSINOPHILS IN AIRWAY TISSUE

| Time of Treatment | Saline | OVA | Zileuton | HK-X |
|---|---|---|---|---|
| 28 days | 1.0 | 44.8 | 15.8 | 14.2 |

2. Other Inflammation Cells

Other inflammation cells indicates a non-specific inflammatory response following the introduction into the airway of a foreign protein. Lymphocytes were recruited into the airways, but were virtually absent in control groups. Neutrophils were recruited following OVA challenge in boot sham-sensitized and OVA-sensitized mice, although greater numbers were presented in the airways of the OVA sensitized group. Peculiar multinucleate giant cells (fused macrophages) having crescents of nuclei around the periphery of their extensive cytoplasm, were occasionally seen. Both Langhans giant cells and globule leukocytes were observed only in animals sensitized and challenged with OVA. They were usually present in the connective tissue associated with larger airways. Plasma cells were occasionally seen in the proximity of the airways and in local lymphoid tissue.

3. Airway Plug (TABLE 3)

Mucin: There was no difference among the three groups with the same treatment but difference time course ($P>0.05$). The OVA-treated group had a higher score than that of the groups treated with saline, Zileuton ($P<0.05$) and HK-X compound.

TABLE 3

MUCUS PLUG SCORE IN AIRWAYS

| Time of treatment | Saline | OVA | Zileuton | HK-X |
|---|---|---|---|---|
| 28 days | 0.7 | 2.8 | 1.3 | 1.4 |
| % of plug of airway | >5% | 55% | 16% | 19% |

Asthma is a chronic inflammatory condition of the airways. In humans, once it is established, the airway hyperresponsiveness can remain stable for years. It persists apparently in the absence of allergen inhalation, detectable airway inflammation or epithelian desquamation. Thus, it may become permanent due to irreversible (or at least slowly reversible) alterations in airway ultrastructure.

In mild asthmatics, these episodes or "attacks" are relatively infrequent and well-treated (reversed) with inhaled bronchodilators. Its intensity of an underlying, distinctive and chronic airway inflammation is associated, and seemingly linked, to more frequent, intense and prolonged attacks that are less reversible by bronchodilators. The reasons for this have become increasingly clear in recent years. The inflammation, which consists principally of an activated or primed infiltrate of Th2-lymphocytes, eosinophils, mast cells, and possibly platelets, causes an expansion of the perivascular ((interstitial) spaces and release of mediators/growth factors, which cause thickening of the basement membrane, epithelial damage and shedding, production of viscous mucus, and hyperplasia, priming as well as partial constriction of airway smooth muscle. All of these outcomes support an increase in airway responsiveness, which lowers the threshold for response to environmental stimuli, thus making attacks more frequent and robust.

All the above morphological changes will directly and strongly affect the pulmonary functions. In experiments on acute asthmatic mouse model and on long-term asthmatic mouse model, the significant pathophysiological changes of pulmonary functions have been observed to support the above morphological changes. Allergen inhalation was found to increase eosinophils and mast cells expression on airway and alveolar endothelium and epithelium, as well as inducing E-selection expression only on airway endothelium, and both the eosinophil infiltration and increase in airway responsiveness, and the other types of inflammatory cells (globule leukocytes and multinucleate giant cells (fused macrophages) of the Langhans type), which indicated non-specific inflammatory reaction within the asthmatic lungs.

Compound HK-X inhibits mucus accumulation in the airway of OVA-treated (OVA) and control mice. The distribution of mucus occlusion of airways was determined from sham-sensitized and saline-challenged mice (saline, n=4), and OVA-sensitized/challenged mice in the absence (OVA, n=4) or presence (HK-X/OVA, n=8) of HK-X treatment. Mucus occlusion of airway diameter was assayed morphometrically as following: 0, no mucus; +, ~10% occlusion; ++, 30% occlusion; +++, ~60% occlusion; ++++, ~80% occlusion. 10 airways randomly distributed throughout the lungs of each mouse were assessed for mucus occlusion morphometrically.

Figures 6A, 6B:
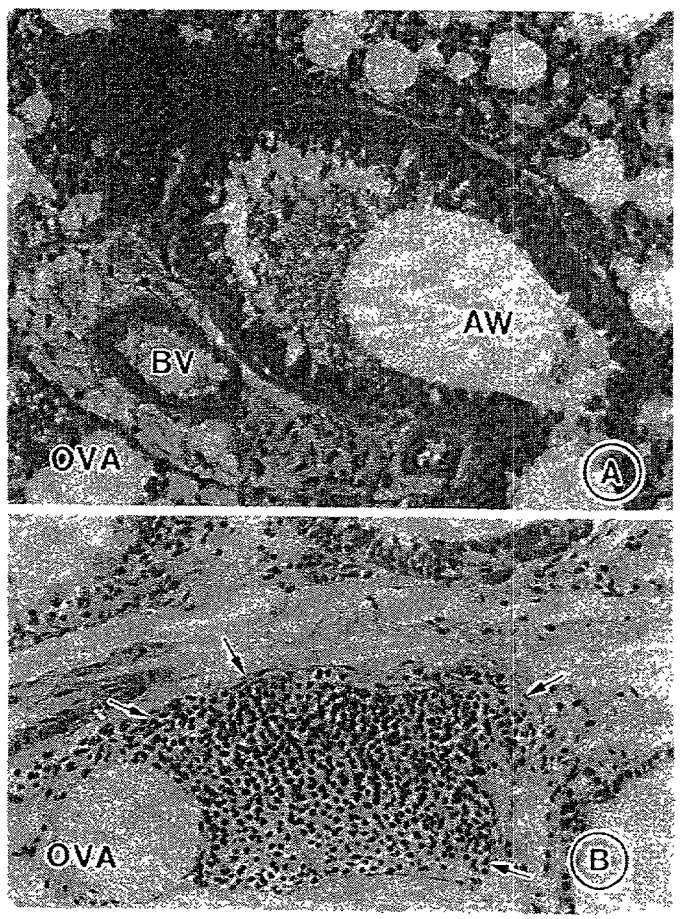
FIGS. 6A-6D are micrographs illustrating the comparative histopathology of a treatment with a compound of the present invention inhibiting the OVA induced asthma in treated mice and control mice.
Figures 6C, 6D:
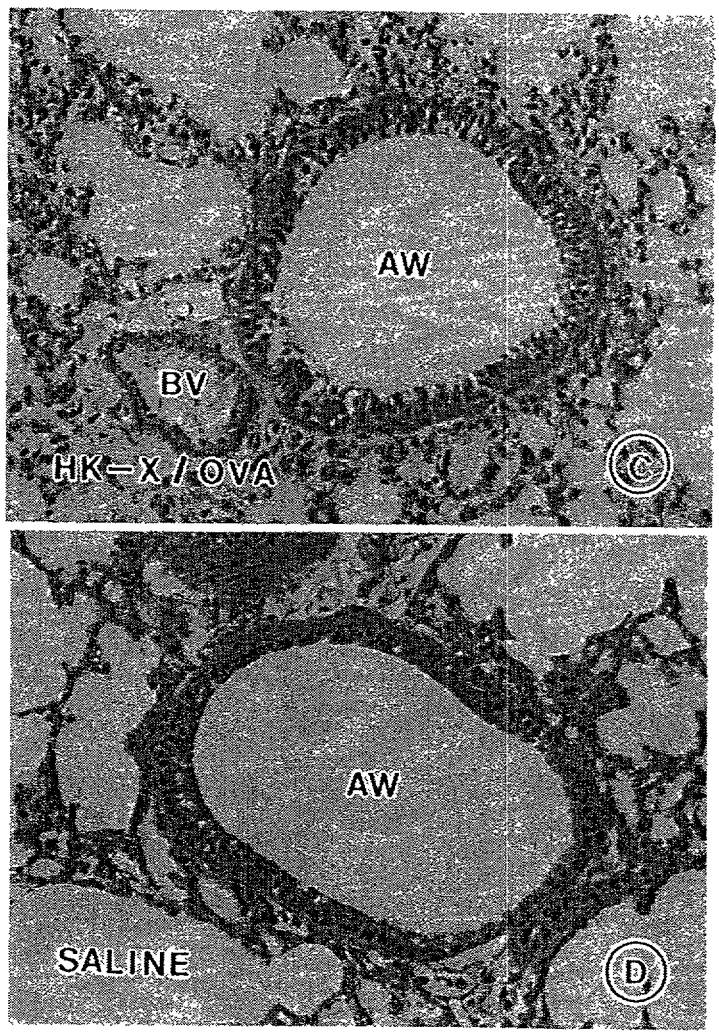

FIGS. 6A-6D provide visual histologic evidence of the ability to of Compound HK-X to inhibit degranulation of mast cells in asthma induced rats using OVA and thereby the effect of treating asthma with Compound HK-X. FIG. 6A shows an abundance of secreted mucus in the lumen of the airway (AW) of OVA sensitized/challenged mice. FIG. 6B shows massive infiltration of the interstitial tissue by eosinophils and other inflammatory cells (noted by arrows). FIG. 6C shows that airway mucus release in the airway (AW) lumen is markedly reduced when Compound HK-X inhibitor is given before i.n. OVA. The infiltration of the interstitial tissue by eosinophils is also reduced after Compound HK-X treatment compared to OVA-challenge alone (compare FIG. 6C with FIGS. 6A and 6B). FIG. 6D shows that the airway (AW) is clear of mucus and cells in Saline-treated control mice. The bronchial epithelium is infiltrated with connective tissue cells but no leukocytes are present in the peribronchial interstitial space.

Airway macrophages showed signs of gross activation that resembled those reported in macrophages recovered in BAL fluid from allergen-challenged lungs of asthmatics (*Am. Rev. Respir. Dis.* 1987; 135: 433-440). Macrophages and dendritic cells function as antigen-presenting cells in lung and may lead, directly or indirectly, to the secretion of cytokines able to initiate phenotypic changes in airway epithelium and its peripheral sites. The stimulation of the chronic inflammation of the airway may directly induce the proliferation of airway epithelium and fibroblasts, and the consequent collagen deposit around these areas. Activated macrophages and dendric cells remained high in the area in comparison with the other inflammatory cells during the late-stage challenges.

The airway epithelium was thickened, due largely to a marked goblet cell hyperplasia, particularly in the larger airways, but also in small and even terminal bronchioles. The ratio of goblet cells to normal, columnar, ciliated cells was greatly increased compared with control groups. Whereas control airways (both small and large) had only the occasional goblet cells, section from OVA-challenged lungs showed that 100% of large airways and part of small airways contained goblet cells as up to 88% of the total airway epithelial cells. In lungs that had not been lavaged, mucus could be seen within the goblet cell and in some airways, occasionally completely occluding the lumen. Cellular debris was enmeshed in these mucus plugs. Goblet cell hyperplasia was not seen in control groups and, therefore, could not have been due to a "non-allergic" effect of OVA, or to the intratracheal dosing technique. Some of the goblet cells in the small airways are free of this feature, indicating perhaps that the distribution of OVA within the respiratory tree had not been uniform.

Figure 7:
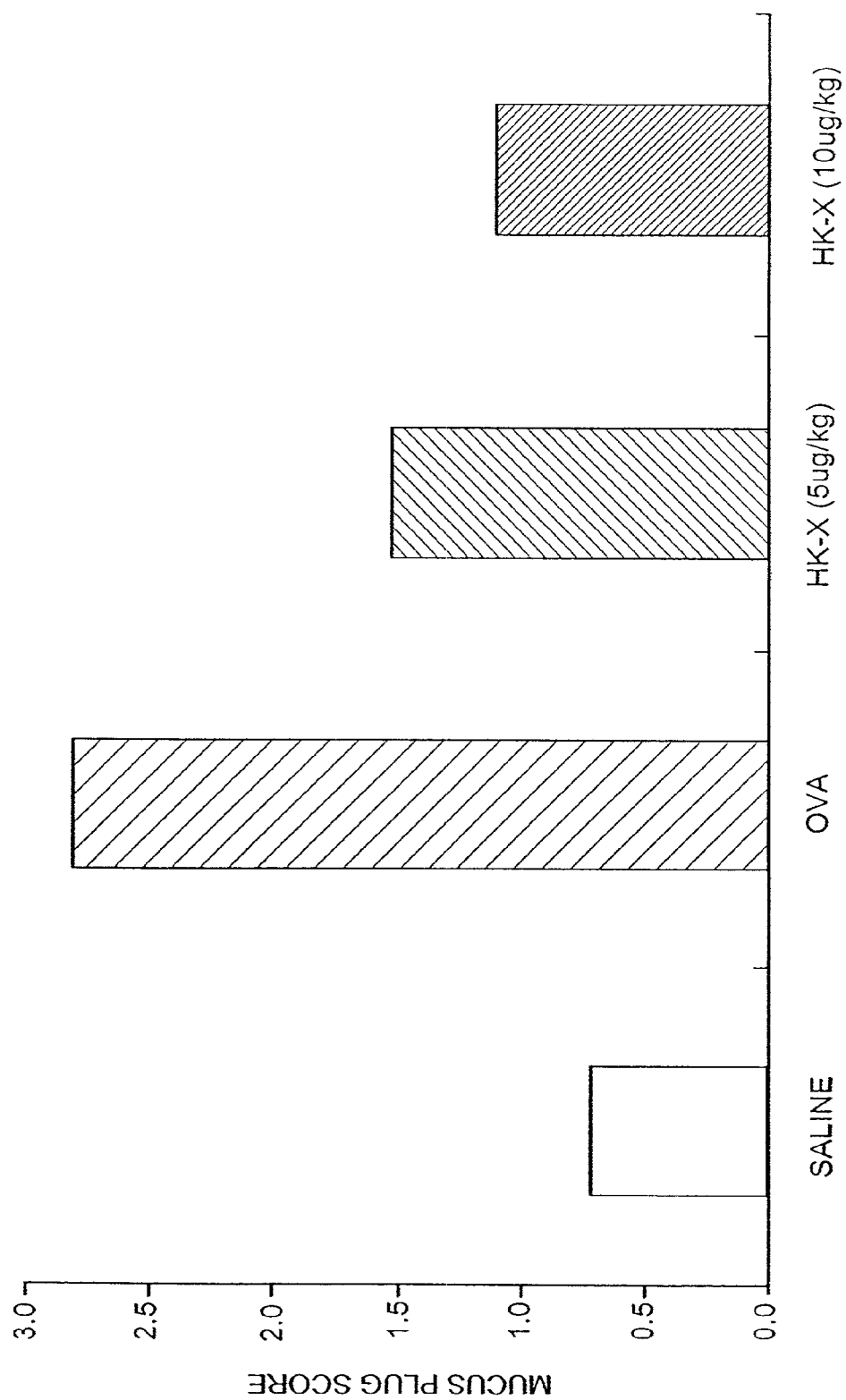
FIG. 7 is a histogram showing the results for treatment in accord with the present invention on formation of mucus plugs in a murine asthma model.

FIG. 7 is a histogram of the results for treatment with Compound HK-X at doses of 5 μg/kg and 10 μg/kg on formation of mucus plugs in this murine asthma model. Both doses significantly reduce the mucus production in small airways.

Asthma is characterized by a complex inflammatory response of airway eosinophilia, edema, mucus hypersecretion, bronchial epithelial injury and hyperreactivity. Inhaled allergen challenge in allergic asthmatics provokes an immediate airway hypersensitivity reaction, an early airway response (EAR), that is frequently followed several hours later by a delayed airway reaction, a late phase airway response (LAR). After recovery from LAR, there is an increase in acquired airway hyperreactivity (AHR) to agents such as methacholine that may persist for several days. The EAR occurring shortly after allergen challenge is likely secondary to the action of bronchoconstrictor molecules released by human lung mast cells as a consequence of IgE-mediated degranulation.

IgE-mediated mast cell degranulation is the primary event in the pathogenesis of such allergic disorders as allergic rhinitis, asthma, and anaphylaxis. In atopic individuals, the intracutaneous injection of specific allergen results in an immediate wheel and flare response that is characterized by the release of histamine and formation of lipid mediators at the skin test site. The early skin response is followed by a late skin reaction occurring 6 to 12 hours later. This late allergic skin reaction is characterized by an inflammatory response consisting of perivascular edema and cellular infiltration by eosinophils and other inflammatory cells (e.g., neutrophils, monocytes, and basophils). Similar dual phase IgE dependent reaction such as, early and late rhinitis or asthmatic responses occurs in the upper and lower airways of atopic individuals after local challenge with specific allergen. Mast cells are located in close proximity to the alveolar surface to blood vessels. Mast cells may influence the pulmonary vasculature by affecting tone or by promoting an inflammatory response. Mast cells activated by immunologic or non-immunologic stimuli degranulate and release a multitude of preformed and newly generated mediators such as histamine, neutral proteases, peroxidase, $O_2$, PAF and eicosanoids (e.g., LTB4, LTC4, PGD2, TXA2) and cytokines (e.g., IL-4, IL-5, TNFa), which may mediate lung inflammation.

The above-described murine model reproduces key features of human asthma. Late-phase allergen-specific pulmonary disease was induced in normal BALB/c mice using ovalbumin (OVA) as allergen. One protocol includes immunization of mice with i.p. OVA on days 1 and 14, and intranasal (i.n.) administration of OVA on days 14, 25, 26, and 27. On day 28, OVA-treated mice display a disease strikingly similar to allergen induced asthma including: (1) increased circulating levels of total and OVA-specific IgE, (2) increased release of LTB4 and LTC4 in BAL fluid, (3) a marked eosinophil influx into BAL fluid and the pulmonary parenchyma, (4) mucus occlusion of small airways, (5) increased expression of T-helper cell type 2 (Th2) cytokines (IL-4, IL-5, and IL-13) and decreased expression of Th1 in cytokines (IL-2 and IFN-y) in bronchial lymph node tissue, (6) pulmonary hyperreactivity, as assessed by a significantly more rapid decline in airway conductance and dynamic compliance with increasing doses of methacholine compared to control mice.

The mouse is also susceptible to development of IgE-mediated allergic airway responses. The late-phase influx of eosinophils is reproduced in this murine model in which allergic airway disease develops after ovalbumin inhalation in mice previously sensitized to ovalbumin intraperitoneally. Increased airway responsiveness to methacholine or acetylcholine challenge also occurs in immunized mice following airway exposure to antigen.

In a mouse model of allergen-induced airway inflammation, the role of mast cell in airway eosinophil infiltration, mucus release, and hyper-responsiveness to methacholine was examined. The small peptide HK-X was found to be a key to the prevention of the mucus release by the mechanism of prevention of mast cell degranulation and eosinophil nfiltration of the airways.

Materials were used as described above. Mice received an i.p. injection of 0.2 ml (100 ug) of OVA complexed with aluminum potassium sulfate (alum) on day 0 and 14. On days 14, 25, 26, and 27, mice were anesthetized with 0.2 ml i.p. of ketamine (0.44 mg/ml)/xylazine (6.3 mg/ml) in normal saline before receiving an intranasal (i.n.) dose of 100 ug OVA in 0.05 ml normal saline on days 25, 26, and 27. Lung tissue was obtained 24 hours after the last i.n. challenge on day 28. The control group received normal saline with alum i.p. on days 0 and 14 and normal saline without alum i.n. on days 14, 25, 26, and 27. To assess the effect of HK-X inhibition on OVA induced asthma, HK-X (10 ug/ml) was given i.n. 30 minutes before each i.n challenge on days 25, 26, and 27.

After tying off the left lung at the mainstem bronchus, the right lung was ravaged three times with 0.4 ml of normal saline, Bronchoalveolar lavage (BAL) fluid cells from a 0.05 ml aliquot of the pooled sample were counted using a hemocytometer and the remaining fluid centrifuged at 4° C. for 10 minutes at 200 g. After resuspension of the cell pellet in normal saline containing 10% BSA, BAL cell smears were made on glass slides. To stain eosinophils, dried slides were stained with Discombe's diluting fluid (0.05% aqueous eosin and 5% (v/v) acetone in distilled water) for 5-8 minutes, rinsed with water for 0.5 minutes and counterstained with 0.07 methylene blue for 2 minutes.

Following BAL, the trachea and left lung (upper and lower lobes) were obtained and fixed in 10% buffered formalin solution at 20° C. for1S hours. After the tissues were processed and embedded in paraffin, the tissues were cut into 5 µm sections and stained with Discombe's solution and counterstained with methylene blue as described above or stained with Hematoxylin and eosin. The eosinophil number per unit airway area (2200 µm$^2$) was determined by morphometry as previously described. Airway mucus was identified by a variety of staining methods, i.e., methylene blue, Hematoxylin and eosin, mucicarmine, toluidine blue, alcian blue, and alcian blue/periodic acid Schiff (PAS) reaction. Mucin was stained with mucicarmine solution; metanil yellow counterstain was employed. Mucin and sialic acid-rich non-sulfated mucosubstances were stained metachromatically with toluidine blue, pH 4.5. Acidic mucin and sulfated mucosubstances were stained with alcian blue, pH 2.5; nuclear fast red counterstain was used. Neutral and acidic mucosubstances were identified by alcian blue, pH 2.5 and PAS reaction. The degree of mucus plugging of the airways (0.5~0.8 mm in diameter) also was assessed by morphometry. The percent occlusion of airway diameter by mucus was classified on a semiquantitative scale from 0 to +++++. The histologic and morphometric analyses protocol design were performed by individuals blinded to the protocol design.

Mucus glycoproteins in BAL fluid were assayed by slot blotting and PAS staining as described. Nitrocellulose membranes (0.2 um pore size; Schleicher & Schuell, Keene, N.H.) were wetted in distilled water and then in normal saline before placement in a Minifold II 72-well slot blot apparatus (Schleicher & Schuell). The BAL fluid samples (0.05 ml) and aliquots (0.05-0.75 ml) of a stock solution (2 ug/ml) of human respiratory mucin glycoprotein were blotted onto the nitrocellulose membranes by water suction vacuum, and mucus glycoproteins were visualized by PAS reaction. Reflectance densitometry was performed to quantitate the PAS staining. The images were captured and digitized by a ScanJet IIcx Scanner with HP DeskScan II software (Microsoft Windows TM Version) (Hewlett Packard, Palo Alto, Calif.). This system was linked to a DellDimension XPS P90 computer (Dell Corporation, Austin, Tex.) employing Image-Pro Plus, Version 1.1 for Windows TM software (Media Cybernetics, Silver Spring, Md.). The images were assessed on a 256 gray level scale using a Dell UltraScan 1 7ES monitor with extra high-resolution graphics mode (1280×1024 pixels, 78.9-kHz horizontal scanning frequency, 74-Hz vertical scanning frequency). The integrated intensity of the PAS reactivity of the BAL samples was quantitated by comparison to the standard curve for human respiratory mucin.

I.p. immunization with OVA results in detectable levels of OVA-specific IgE in the blood of BALB/C mice. Indirect ELISA was employed to determine OVA-specific IgE serum antibody titers. ELISA plates (ICN, Costa Mesa, Calif.) were coated with OVA (20 mg/ml) diluted in 0.1 M NaHCO, buffer pH 8.3 and incubated at 4 degrees for 18 hours. After washing three times, the plates were incubated with 1% BSA in PBS, pH 7.4, at 37 degrees C. for 2 hours. Serial dilution of the serum samples in 1% BSA/PBS buffer were added to the plates and incubated at 4° C. for 18 hours before washing again. The wells were incubated with HRP (horse radish peroxidase) conjugated rat anti-mouse IgE monoclonal antibody (Pharmingen, San Diego, Calif.) diluted in 50% goat serum (Gibco-BRL, Gaithersburg, Md.)/PBS buffer for 2 hours at room temperature. 3,3',5,5'-tetramethylbenzidine substrate was used to develop the wells with absorbance determined at 610 nm. The internal standard in each assay consisted of pooled serum from OVA-immunized BALB/c mice.

The pulmonary function data were evaluated by analysis of variance (ANOVA) using the protected least significant difference method (Statview II, Abacus Concepts, Berkeley, Calif.). This method uses a multiple t-statistic to evaluate all possible pairwise comparisons and is applicable for both equal and unequal pair sizes. The other data are reported as the mean+SE of the combined experiments. Differences were analyzed for significance ($p<0.05$) by Student's two-tailed t-test for independent means.

Results

Allergen-Specific IgE Production. OVA-specific IgE (12.9+0.3 U/ml, n=5) was detected on day 28 in the blood of mice given i.p. OVA and alum on day 0 and 14 and i.n. OVA on day 25, 26, and 27. In contrast, control mice treated with i.p. saline and alum and i.n. saline (n=6) had no detectable anti-OVA IgE.

Allergen-induced Airway Inflammation. To assess allergen-induced airway inflammation histologically, lung tissue and BAL fluid were obtained on day 28, 24 hours after the last of 3 sequential i.n. OVA challenges on days 25, 26, and 27. By light microscopy, prominent infiltration of the bronchial interstitium by eosinophils was observed (FIG. 8C). Eosinophil influx into the bronchial epithelial mucus layer (FIG. 9D) and the BAL fluid was also noted.

61.0+5.0% (n=10) of the BAL fluid cells were eosinophils in OVA-sensitized/challenged mice compared to 0.8+0.3% (n=10) in saline-challenged control animals (p=0.0001).

Mucus occlusion of the airways occurred in immunized mice after bronchial challenge with OVA (FIG. 10). Airway mucus release in both lower (FIG. 9B) and upper (FIGS. 9C, 9D) pulmonary airways was identified by separate histochemical staining procedures: mucin by mucicarmine stain, acidic non sulfated mucosubstances by toluidine blue, acidic sulfated mucosubstances by alcian blue (FIG. 10), and neutral and acidic mucosubstances by alcian blue/PAS reaction. Airway lumen occlusion by mucus was greater in the lower airways. These inflammatory changes were absent in i.n. saline-challenged control animals that had treated i.p. with either saline (FIG. 8B) or OVA (not shown) with alum.

Figures 9A, 9B:
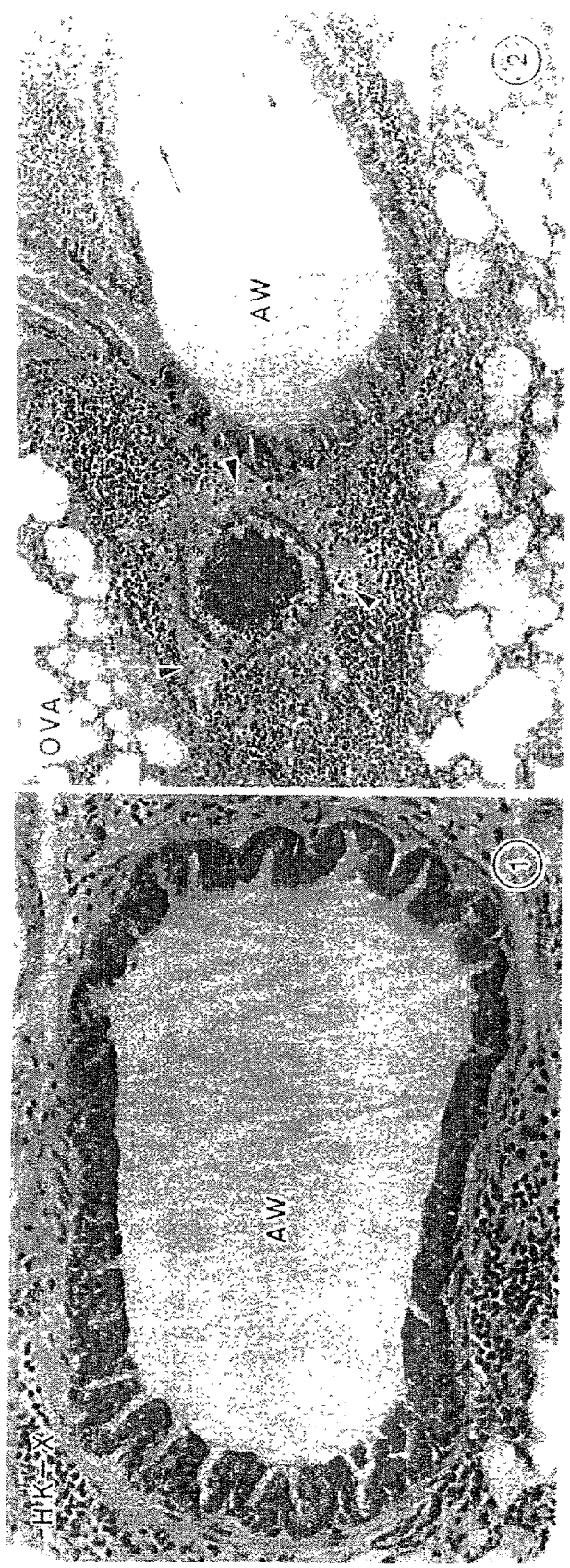
Figures 10A, 10B:
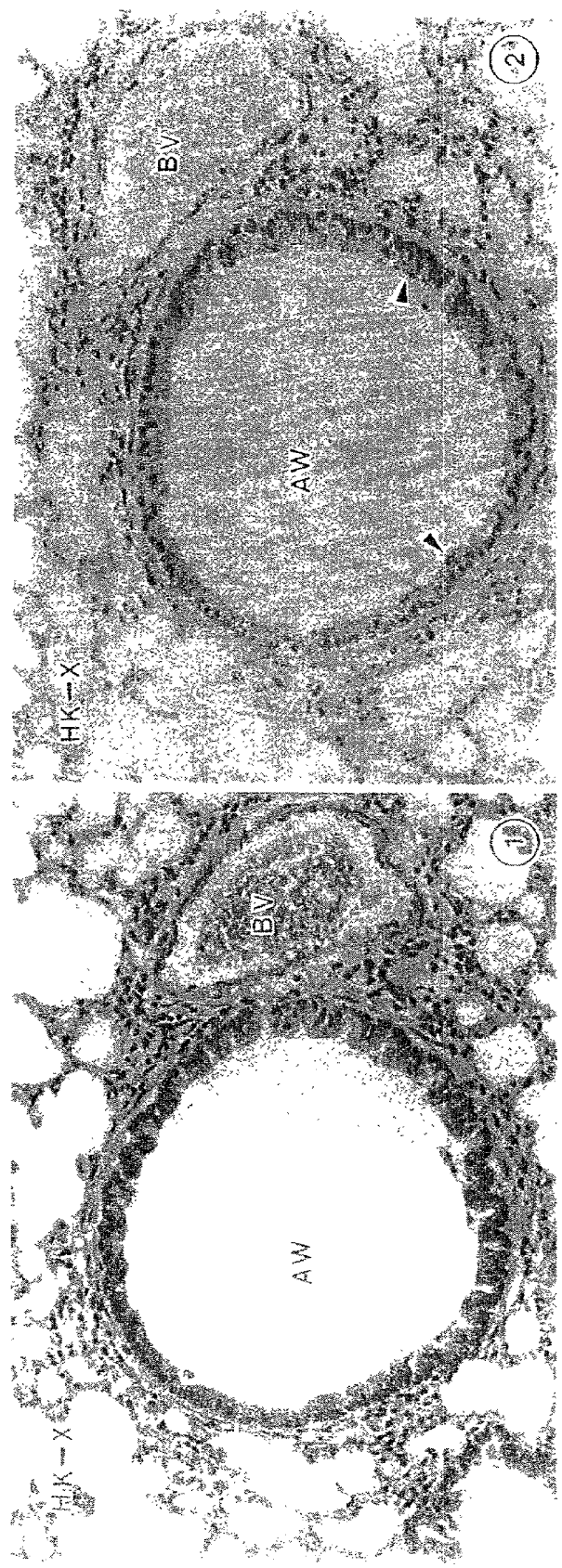
FIGS. 10A-10D show the histopathology of lung tissues of a third group of mice treated in accord with the present invention after induced with asthma.

HK-X Inhibition Blocks Eosinophil Infiltration and Mucus Accumulation in Airwaves. Inflammation inhibition by HK-X markedly reduced eosinophil influx into the lung tissue and BAL fluid of OVA sensitized/challenged mice and also prevented airway mucus release in these animals (FIGS. 8A, 9A, 10A).

Figure 11:
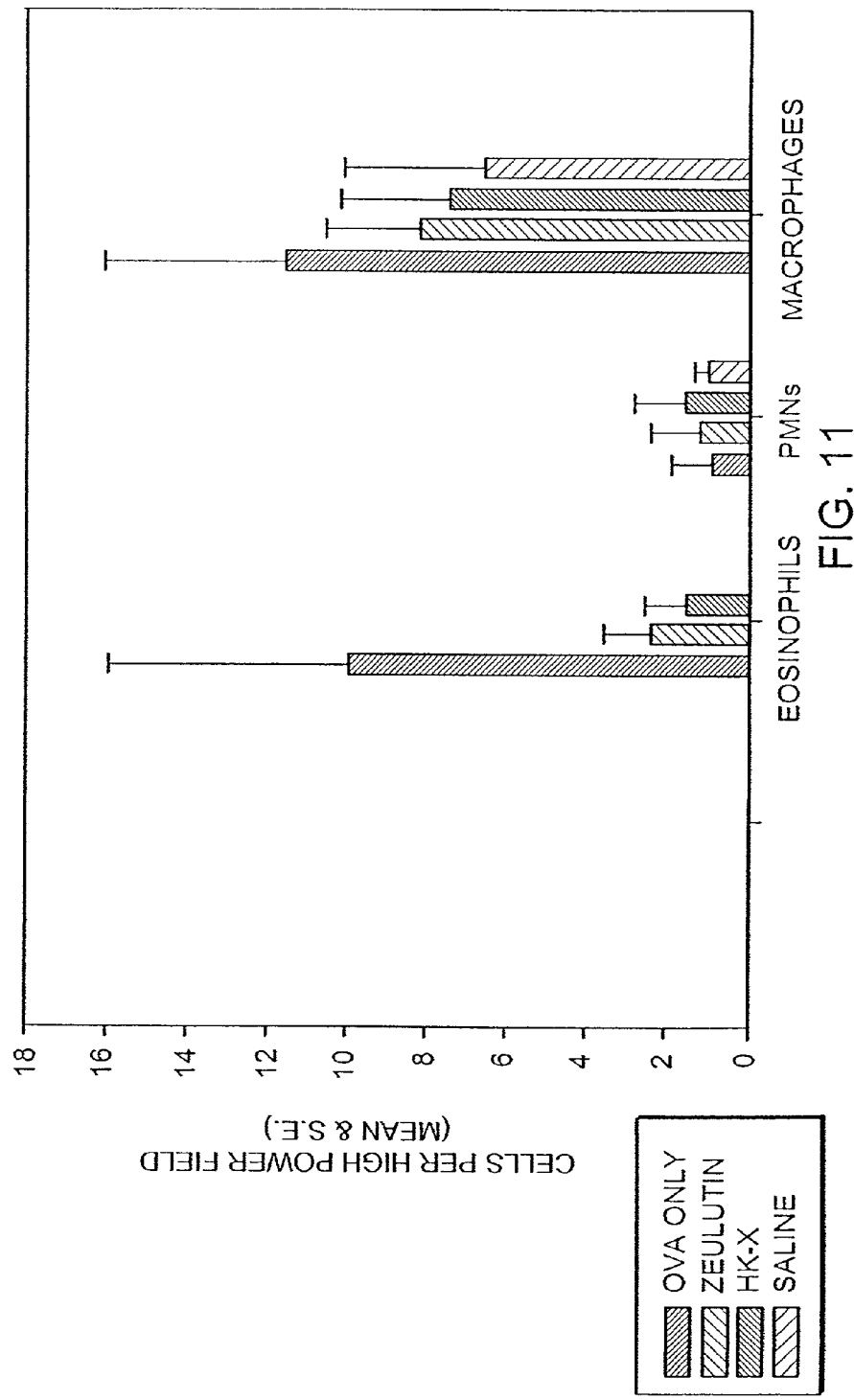
FIG. 11 is a graph illustrating the distribution of inflammatory cells in the aveoli of lungs recovered from OVA-induced asthmatic mice

Eosinophil Infiltration. By morphometric analysis, the eosinophil influx into the lung interstitium was reduced 90% by HK-X treatment ($p<0.006$ compared to OVA without HK-X) (FIG. 11). The SLO Zileuton decreased the number of eosinophils in the BAL fluid by 82% ($p<0.004$ compared to OVA Zileuton (FIG. 11). The number of eosinophils in the BAL fluid from the OVA-sensitized/challenged mice treated with the HK-X was determined as $0.57+0.11\times10^5$ and OVA-immunized/saline-challenged as $0.16+0.03\times10^5$ (control mice). Zileuton similarly decreased eosinophils recovered in the BAL fluid of OVA-sensitized/challenged mice by 89% (p=0.0128 compared to OVA without zileuton; data not shown). Vehicle controls (Trappsol TM for Zileuton studies,) did not affect the lung eosinophil infiltration observed in OVA sensitized/challenged mice.

Mucus Accumulation. Cross-sections of the upper and lower lobes of the left lung of OVA-treated and control mice were examined by light microscopy for mucus accumulation in the airways. By morphometric analysis, 68% of the airways of control mice treated with saline had no evidence of airway mucus release, and the remainder had only a small mucus layer observed. In contrast, OVA-immunized/challenged mice had morphologic evidence for widespread mucus plugging of the airways. The majority (74%) of the airways of the OVA-treated mice had at least 30% occlusion of the airway lumen by mucus; 22% of the airways of these mice had 80% or greater mucus occlusion. When the amount of mucus glycoprotein recovered in the BAL fluid was quantitated (FIG. 12), seven-fold increase in airway mucin was demonstrated in OVA-treated mice compared to control mice (p=0.00001 OVA versus saline). HK-X treatment blocked the airway mucus release in the OVA-treated mice (FIGS. 8A, 9A, 10A).

Figures 8A, 8B:
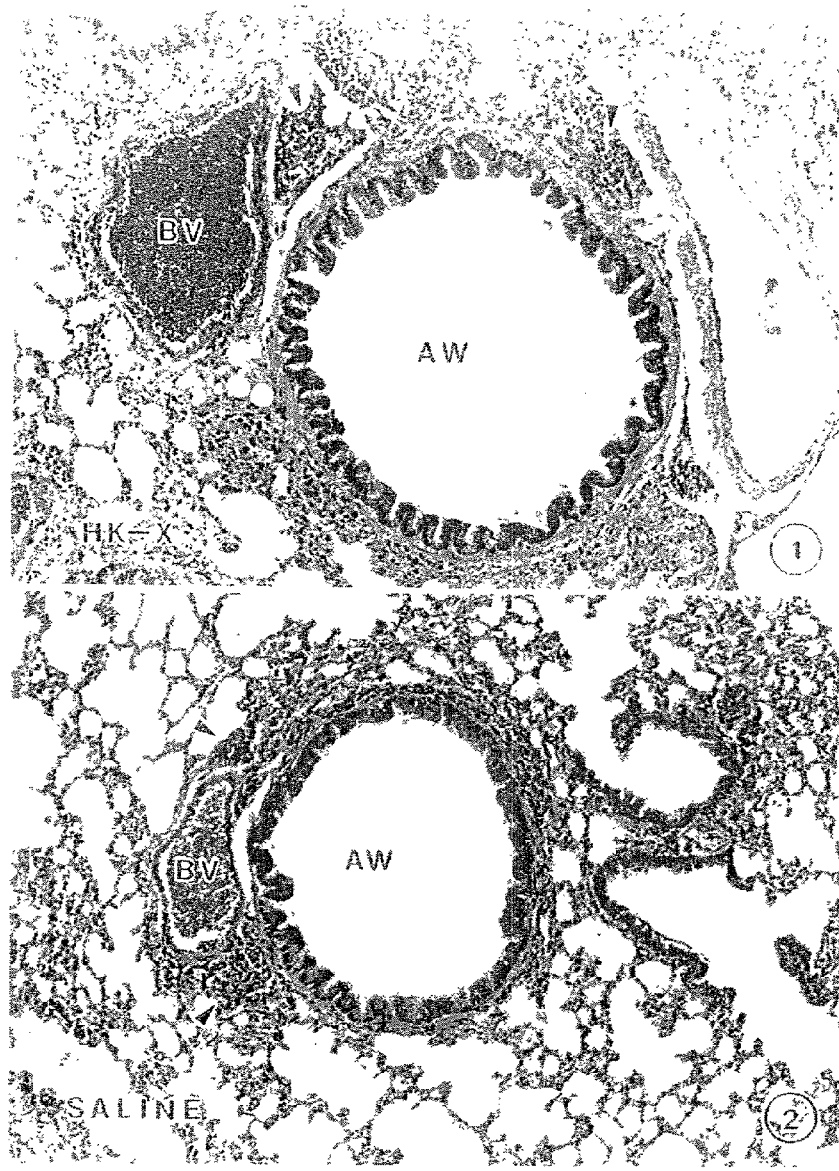
FIGS. 8A-8C show the histopathology of lung tissues of mice treated in accord with the present invention after induced with asthma.
Figure 8C:
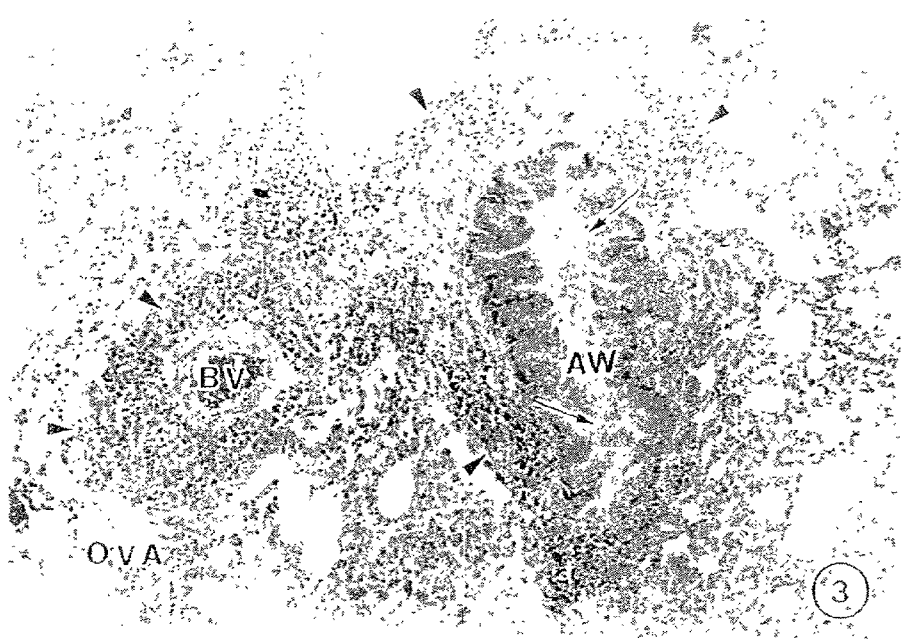

FIGS. 8A-8C show the histopathology of the lung tissue and illustrates the effectiveness of the treatment of the OVA induced mouse asthma by the small peptide (HK-X) (n=8) at each group of animals. FIG. 8A is a picture of a HK-X treated mouse lung, which shows the normal characteristics of the features of airway (AW) and blood vessel (BV). There is very little number of cells located in the periphery of the airway tissues (arrowheads)(H & E stain, X12). FIG. 8B is a picture of a mouse that received only saline injections used as a normal control. The airway and the blood vessel are normal appearances. A few cells are seen in the airway tissue (arrowheads) (H & E stain, X120). FIG. 8C is a picture of an OVA immunized animal, which shows a profound affect by characteristics of eosinophil and T-cell, monocyte, and macrophage infiltration in the airway tissue (arrowheads). The airway is plugged by the mucus and cells (arrows) (H & E stain, X120).

FIGS. 9A-9D show the histopathology of lung tissues treated with small peptide (HKX) after induced with asthma in mice. This group of data are obtained from another group of mice. Histopathological evidence of the effectiveness of the HK-X compound in treatment of asthma in mouse model is illustrated. The HK-X compound prevents the airway mucus secretion by OVA challenge daily for a total of three days.

Also the HK-X reduces the cellular infiltration during the episode of asthmatic attack. The mice were immunized with OVA intravenously and intranasally at day 1 and day 14. In day 25, 26, and 27 the mice were challenged with OVA or 30 minutes prior to challenge mice were received 10 μg HK-X intranasally.

FIG. 9A is a micrograph of a medium-sized airway (AW) and is representative of a typical HK-X treated mouse lung. The HK-X treated lung shows very little pathological condition as seen in the OVA treated animals. The airway is very clear with very little or no mucus observed in the lumen or on the epithelial cell surface. Very little amount of cellular infiltration in the parenchyma of the airway is seen. The smooth muscle cell layer is uniform in thickness. (H&E stain, X150). FIG. 9B is a picture of an OVA immunized and challenged mouse lung, which shows the typical characteristics of asthma in human: a partial plugged airway (AW) lumen (arrows), a predominant feature of cellular infiltration in the interstitium of airways and blood vessels, and a periphery edema seen in association with blood vessels (arrowheads). (H & E stain, X75). FIG. 9C is a picture at a higher magnification of an airway of asthmatic mouse lung, which illustrates a plugged lumen. Numerous leukocyte cells are located in the basal region of the airway epithelial cell layer (arrowheads). There are many eosinophils are seen in the parenchyma, and the smooth muscle cell layer is uneven in thickness. (H & E stain, X150). FIG. 9D is a picture of a partial longitudinally sectioned airway of an asthmatic mouse lung, which shows the extensive blocking of the airway lumen by released mucus (arrows). The cellular infiltration is very closely located at the area of the epithelial cell layer (arrowheads). The smooth muscle cell layer is distracted by the infiltrating leukocyte cells and a small granuloma is often formed. (H & E stain, X150).

Figures 10C, 10D:
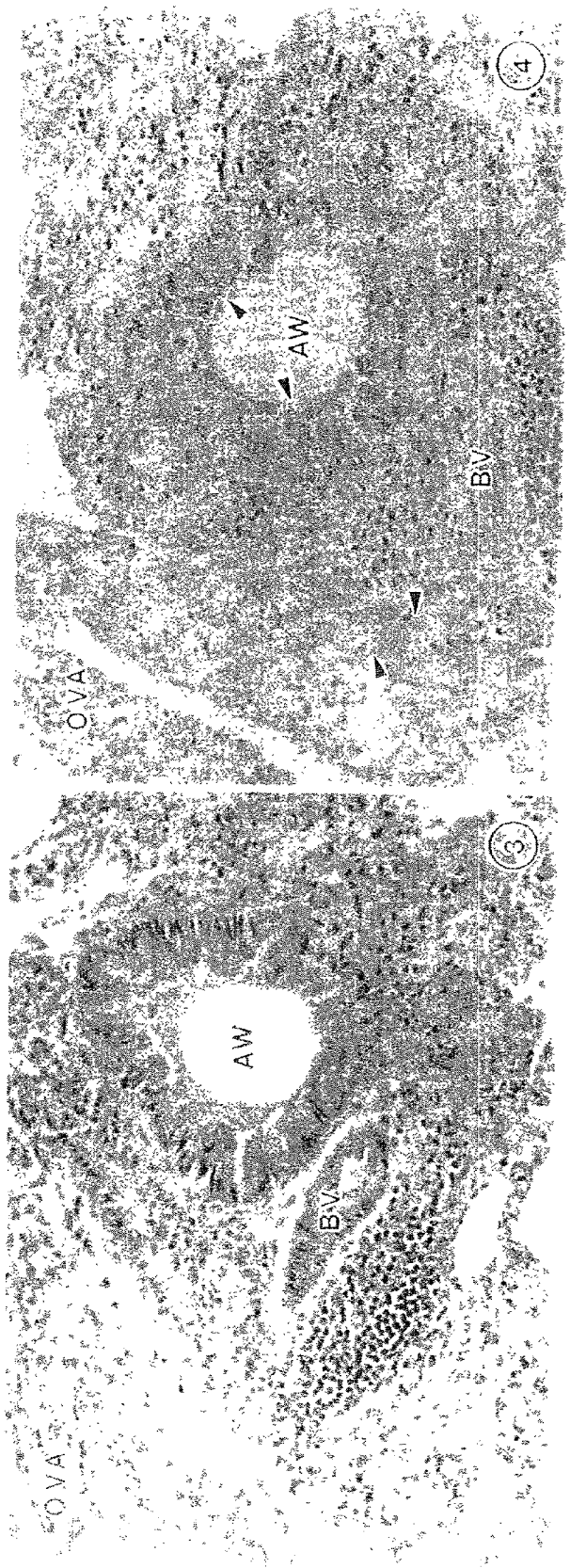

FIGS. 10A-10D illustrate the histopathological data obtained from another group of mice (n=9). Further histopathological and histochemical evidence is seen that the HK-X compound prevents the mucus cell induction by OVA immunization and challenge and reduces the mucus secretion in airways. During asthmatic attack, there is an increase mucus secretion and airway constriction. The production of mucus is evident by the developing of mucus cell in the airways. Using alcian blue stains the sulfated glucosamine glucans to express the mucosubstances. FIG. 10A is a picture of a HK-X treated asthmatic mouse lung, which shows the airway (AW) lumen is empty and no extracellular substance occurred in the lumen. An adjacent blood vessel (BV) is also present. The normal appearance shows no cellular infiltration or edema fluid. (H&E stain, X150). FIG. 10B is a sequential section of the same airway as seen in FIG. 10A, which is stained with alcian blue at pH 2.4 to localize the mucosubstances in epithelial cells. Only a few positive cells are seen in the lumen (arrowheads). A sporadic thin-layer of blue positive substances is evident. (Alcian blue and neutral red stain, X150). FIG. 10C is a picture of an OVA immunized and challenged mouse lung, which shows a constricted airway and mucus secretion in the lumen (arrowheads). Numerous leukocytes are observed in the lung tissue. Many of them are eosinophils. (H & E stain, X150). FIG. 10D is a similar section as shown in FIG. 10C, which is stained with Alcian blue to indicate the muco-substances in the constricted airway. A thick-layer of mucus is seen closely attached to the epithelial surface (arrowheads). There, more blue positive cells are seen, indicating a much higher proportion of mucus cells appeared in the airway lumen. Note a longitudinal small airway filled with mucus also is seen in this section. (Alcian Blue & Neutral Red stain, X150).

Figure 12:
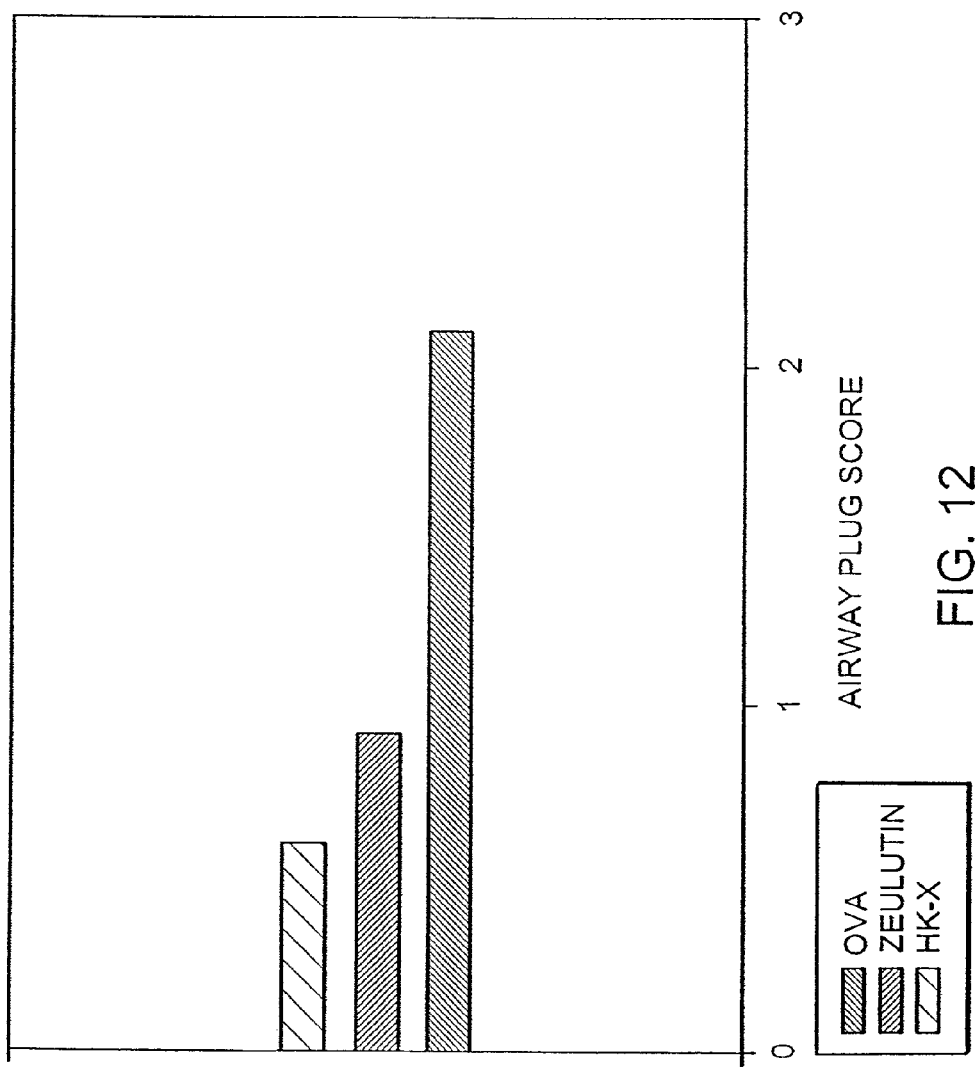
FIG. 12 is a graph illustrating the airway plug score in airways of OVA-induced asthmatic mice.
Figure 13:
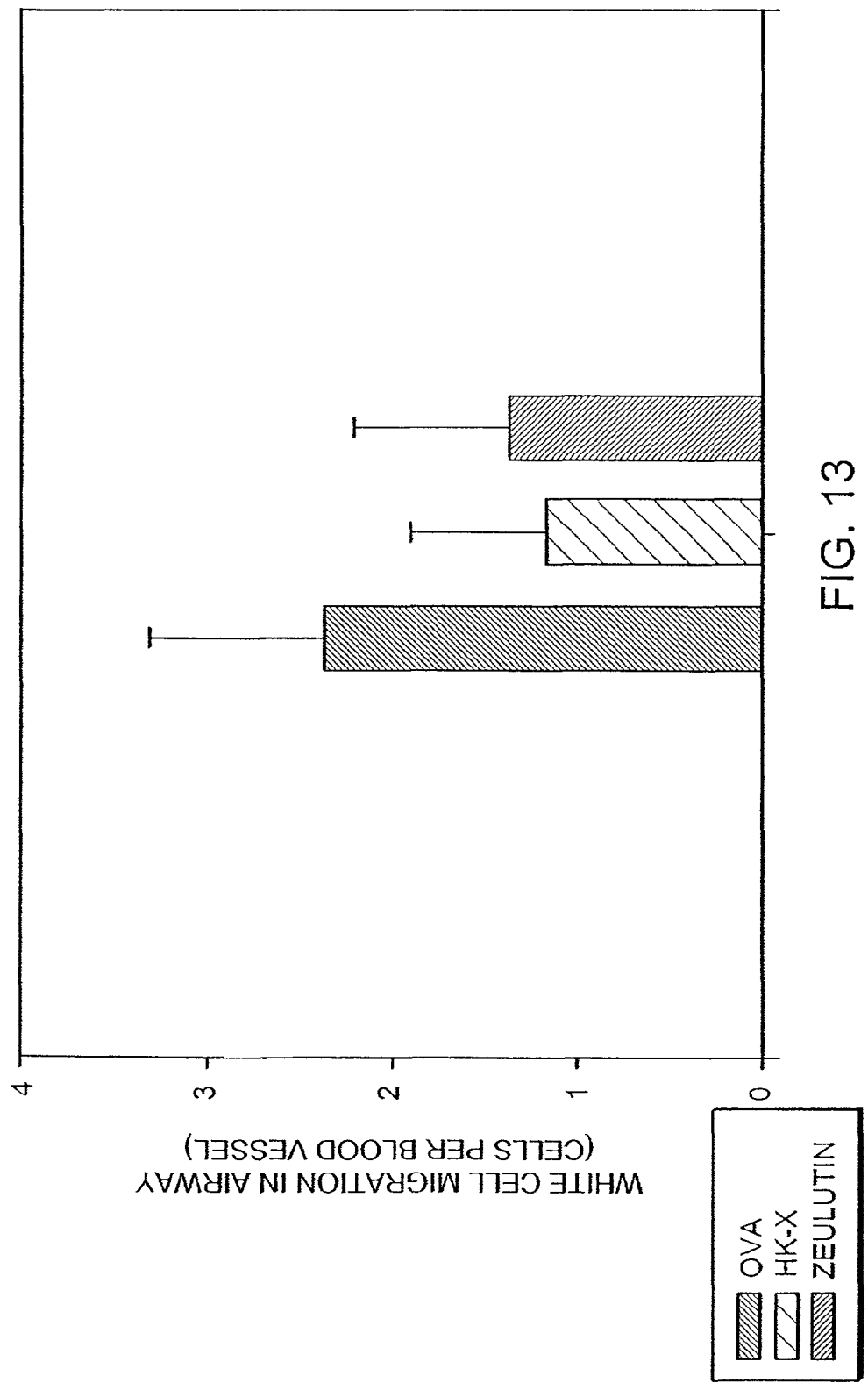
FIG. 13 is a graph illustrating the white cell migration in airways OVA-induced asthmatic mice.
Figure 14:
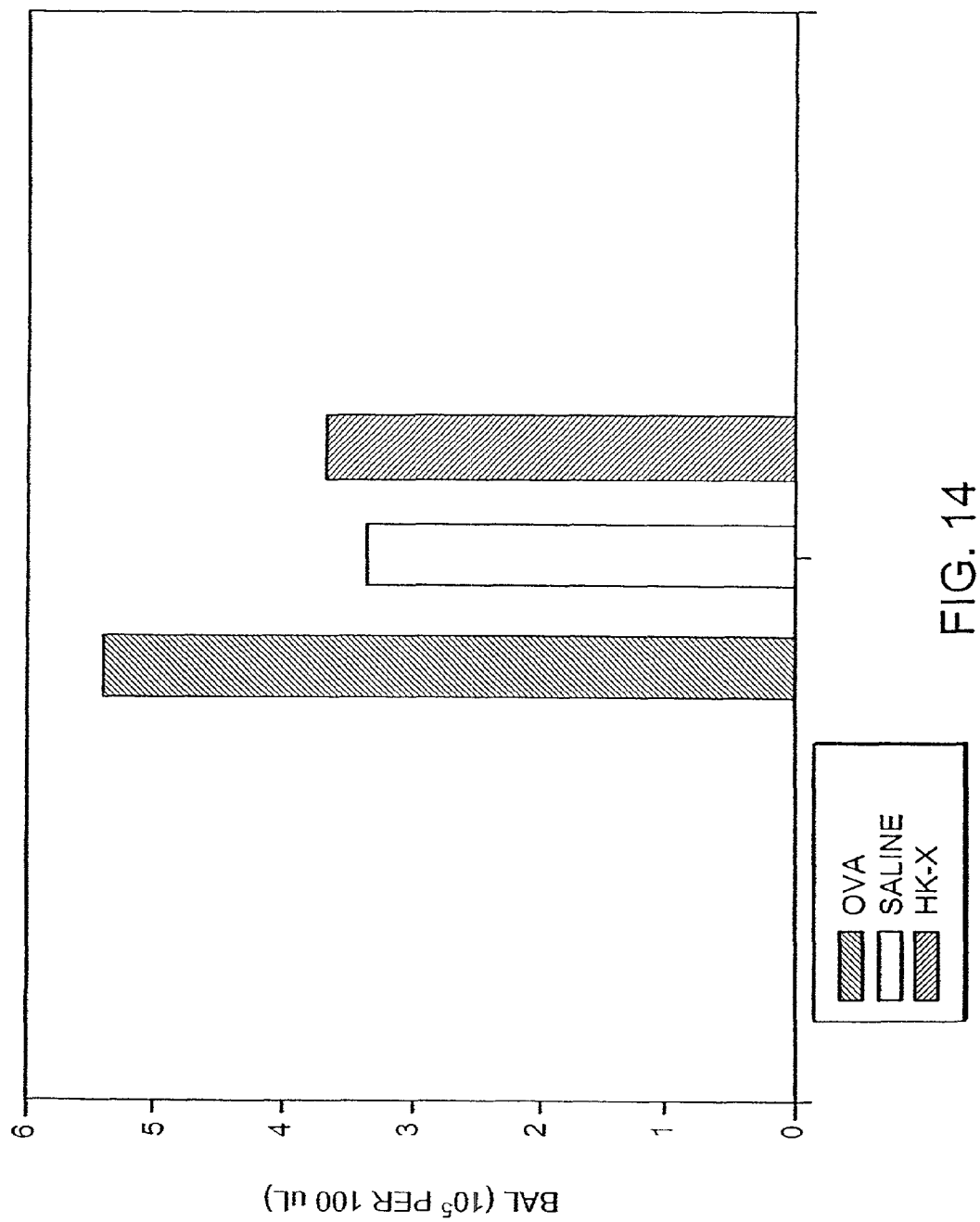
FIG. 14 is a graph illustrating the total cells recovered from lung lavage of OVA-induced asthmatic mice.

FIG. 11 illustrates the distribution of inflammatory cells in the aveoli of lungs recovered from OVA-induced asthmatic mice. FIG. 12 illustrates the airway plug score in airways of OVA-induced asthmatic mice. FIG. 13 illustrates the white cell migration in airways OVA-induced asthmatic mice. FIG. 14 illustrates the total cells recovered from lung lavage of OVA-induced asthmatic mice.

Induced Type II Collagen Arthritis Mouse Model

A mouse model is used to evaluate the effect of the compounds of the present invention on the histological, radiographic and clinical appearance of induced type II collagen arthritis.

Autoimmune diseases cause significant and chronic morbidity and disability. Arthritis in its many forms is representative of a family of autoimmune diseases. In the clinical realm, rheumatoid arthritis (RA) is the most common form of the severe arthrodysplastic disease. All clinicians agree that RA is a progressive disease.

The histopathology of arthritic lesions occurring in murine CIA share enormous similarities to that of RA in human patients. Thus, murine CIA is an accepted model to study potential therapeutic treatments of RA.

Materials and Methods

Mice: DBA/1(2) male mice weighing 25 gms (Jackson Laboratories, Bar Harbor, Me. or B&K Universal, Kent Wash.) are used for this work. This strain of mouse is susceptible to CIA by the injection of heterologous type II collagen. Bovine Collagen (BC), Complete Freund's Adjuvant (CFA) and Incomplete Freund's Adjuvant (ICFA) can be obtained from Sigma Chemical. Antigen for immunization is processed in 0.1 M acetic acid and formulated with CFA or ICFA.

Induction of Arthritis

Immunization protocol: Mice are injected with 100 μg of type II collagen in CFA at predetermined intervals during the study period.

The mice are examined at predetermined intervals for the development of arthritis. Presumptive evidence of arthritis includes swelling and erythema of at least one toe joint on the front and/or rear feet on two consecutive observations.

Confirmatory Diagnosis of Arthritis

Histological examination of joints: The toe joints of animals sacrificed at appropriate intervals are removed, fixed, decalcified, embedded, in paraffin, sectioned, and stained for observation of general cellular and structural features and to detect cartilaginous matrix of the pannus of each joint, as appropriate. The degree of cellularity and areas of inflammation are quantified by using digitization of histological photomicrographs and applying standard area and point counting techniques as described above.

Radiographic evaluation of toe joints is performed to detect the incidence of joint changes after immunization with type II collagen. A mammography imaging system has been modified for this work. The average area of soft tissue (pannus) of the joint is determined by analysis of computer digitized radiographs, along with changes in density of the adjacent hard tissues by comparison with internal standards included with each radiograph. To serve as a baseline control for the changing density of the hard tissues and areas of panni, additional mice are used over the same period and the density and area data compared. The significance of the differences in density and area for control and experimental mice is assessed using paired T-tests at each time point.

Arthritis Evaluation

Animals are observed daily for the onset of arthritis. An arthritis index is derived by grading the severity of involvement of each paw on a scale from 0 to 4. Scoring is based upon the degree of peri-articular erythema and edema, as well as deformity of the joints. Swelling of hind paws is also quantitated by measuring the thickness of the ankle from the medial to the lateral malledus with a constant tension caliper.

Experimental Design

To assess the anti-arthritic effect of Compound HK-X, the routes of administration are selected based on experience with human patients regarding the most appropriate delivery mechanism(s).

Doses of HK-X and Prednisolone: Dosages representing divergent and putatively therapeutic levels of peptide are placed in localized sites, both by transcutaneous (TC) (absorptive) route and by injection into the foot. Direct injection into the intraarticular space is too traumatic likely to produce artifacts. Thus, injection of drug into the footpad (FP) adjacent to the intraarticular space is the chosen methodology. Control mice are also injected with Prednisolone (a potent anti-inflammatory documented in the treatment of experimental and clinical autoimmune diseases) as a positive control.

First, each mouse in a group of ten (plus controls) is injected with collagen daily for 50 days. On days 3 and 18, the mouse is injected with 5 or 10 µg/kg of Compound HK-X in a solution of 0.1 M acetic acid at 1 mg/ml. On day 50, the mouse is exsanguated for histologic studies.

Then, eight groups (A-I) of ten mice each are treated according to the following specific protocol.

Group A is immunized with 1° CFA plus BC, 2° ICFA plus BC and no treatment is given (control).

Group B is immunized with 1° CFA plus BC, 2° ICFA plus BC and prednisolone is administered at 5 mg/kg starting on the day after 2° ICFA plus BC and continued for 20 days.

Group C is immunized with 1° CFA plus BC, 2° ICFA plus BC and Compound HK-X is administered TC at 4 mg/kg (high dose) starting on the day after 2° ICFA plus BC and continued for 20 days.

Group D is immunized with 1° CFA plus BC, 2° ICFA plus BC and Compound HK-X is administered TC at 0.4 mg/kg (low dose) starting on the day after 2° ICFA plus BC and continued for 20 days.

Group E is immunized with 1° CFA plus BC, 2° ICFA plus BC and Compound HK-X is administered TC at 4 mg/kg (high dose) starting on the day after 2° ICFA plus BC and continued for 20 days.

Group F is immunized with 1° CFA plus BC, 2° ICFA plus BC and Compound HK-X is administered TC at 0.4 mg/kg (low dose) starting on the day after 2° ICFA plus BC and continued for 20 days.

Group G is immunized with 1° CFA, 2° ICFA and 10 ml DMSO is administered TC starting on the day after 20 ICFA plus BC and continued for 20 days (control).

Group H is immunized with 1° CFA, 2° ICFA and 10 ml DMSO is administered FP starting on the day after 2° ICFA plus BC and continued for 20 days (control).

Group I is immunized with 1° CFA, 2° ICFA and 10 ml saline is administered FP starting on the day after 2° ICFA plus BC and continued for 20 days (control).

Animals from each group are x-rayed immediately after 2° immunization and immediately prior to sacrifice. Following sacrifice, feet are removed as appropriate and processed for histological examination. The treatment with Compound HK-X is found to reduce the degree of arthritis.

The invention has been described in detail with reference to preferred embodiments thereof. However, it will be appreciated that, upon consideration of the present specification and drawings, those skilled in the art may make modifications and improvements within the spirit and scope of this invention as defined by the claims.

We claim:

1. A method for treating cutaneous inflammation in a mammal, the method comprising administering to the mammal an anti-inflammatory effective amount of a peptide having the formula f-Met-Leu-X where X (SEQ ID NOs: 1, 2 and 3) is selected from the group consisting of Tyr, Tyr-Phe (SEQ ID NO: 1), Phe-Phe (SEQ ID NO: 2) and Phe-Tyr (SEQ ID NO: 3).

2. A method for treating cutaneous inflammation in a mammal, the method comprising administering to the mammal an anti-inflammatory effective amount of a peptide having the formula f-Met-Leu-X where X (SEQ ID NOs: 1, 2 and 3) is selected from the group consisting of Tyr, Tyr-Phe (SEQ ID NO: 1), Phe-Phe (SEQ ID NO: 2) and Phe-Tyr (SEQ ID NO: 3), wherein the cutaneous inflammation is selected from the group consisting of dermatitis, eczema, psoriasis, contact dermatitis, sunburn and aging.

3. The method of claim 1, wherein another active ingredient is administered with said peptide, said active ingredient being selected from the group consisting of anti-leukotrienes, $beta_2$ agonists and corticosteroids.

* * * * *